United States Patent [19]

Blondelle et al.

[11] Patent Number: 5,814,470

[45] Date of Patent: Sep. 29, 1998

[54] MELITTIN-RELATED POLYPEPTIDES, MIXTURE SETS AND LIBRARIES THEREOF

[75] Inventors: Sylvie Blondelle, San Diego; Richard A. Houghten, Solana Beach; Enrique Perez-Paya, San Diego, all of Calif.

[73] Assignee: Torrey Pines Institute for Molecular Studies, San Diego, Calif.

[21] Appl. No.: 888,562

[22] Filed: Jul. 7, 1997

Related U.S. Application Data

[62] Division of Ser. No. 295,086, Aug. 24, 1994, Pat. No. 5,645,996.

[51] Int. Cl.[6] .................................................. G01N 33/53
[52] U.S. Cl. ........................... 435/7.32; 435/7.1; 435/7.2; 435/7.21; 435/18; 436/501; 436/518; 436/531; 436/534; 436/807; 436/815

[58] Field of Search ............................. 435/7.1, 7.2, 7.21, 435/7.32, 18; 436/501, 518, 531, 534, 807, 815; 530/324, 325

[56] References Cited

U.S. PATENT DOCUMENTS 5,645,996  7/1997  Blondelle et al. ........................ 435/7.1

*Primary Examiner*—Lora M. Green
*Attorney, Agent, or Firm*—Welsh & Katz, Ltd.

[57] ABSTRACT

Sets and libraries of sets of polypeptides that are related in sequence to melittin are disclosed that have antimicrobial, hemolytic and hydrolytically catalytic activities, as are processes for making and using the same. A contemplated set is a mixture of equimolar amounts of a polypeptide of SEQ ID NO:2, and more preferably SEQ ID NO:3.

9 Claims, No Drawings

MELITTIN-RELATED POLYPEPTIDES, MIXTURE SETS AND LIBRARIES THEREOF

This is a division of application Ser. No. 08/295,086, filed Aug. 24, 1994, now U.S. Pat. No. 5,645,996.

DESCRIPTION

Technical Field

The present invention relates to the synthesis and use of polypeptide molecules and more particularly, to polypeptide molecules related in sequence to melittin, mixture sets and libraries of such molecules that exhibit antimicrobial, hemolytic and catalytic properties.

Background and Related Art

Synthetic molecules having enzyme-like characteristics of binding a substrate, catalyzing a reaction, and releasing the products to begin a new cycle of reaction (turning over) have been of increasing interest as man has tried to alter or improve upon nature.

One group of such molecules are the catalytic antibodies prepared and studied by Lerner and Schultz and their co-workers. For a review see, Lerner et al., *Science*, 252:659–667 (1991). These molecules utilize the antibody combining site to bind the substrate and catalyze the reaction. Antibodies are, however, very large molecules, having a molecular weight of about 160,000 D for the usually used IgG type, and even F(ab')$_2$ and Fab portions have molecular weights of about 105,000 and 52,000 D, respectively. In addition, antibodies are prepared from living cells, and to date, have not been prepared in bulk chemical amounts.

Polypeptides having a length up to about 50 residues are more readily prepared in bulk quantities. A few of such molecules have recently been reported to possess catalytic activity.

For example, Johnsson et al., *Nature*, 365:530–532 (1993) (See, also, commentary by DeGrado, Ibid., 488–489), reported results using two amphiphilic molecules they named oxaldie 1 and oxaldie 2 that catalyze the decarboxylation of oxaloacetate. These molecules had a length of 14 amino acid residues and were composed of lysine, alanine and leucine, with oxaldie 1 having a free N-terminal α-amino group and oxaldie 2 having its N-terminal α-amino group acylated.

Atassi et al., *Proc. Natl. Acad. Sci., USA*, 90:8282–8286 (1993) reported on two cyclic peptides named ChPepz and TrPepz that were said to mimic the catalytic triad (Ser/His/Asp) active site of α-chymotrypsin and trypsin, respectively. Both cyclic polypeptides contained 28 residues and differed in sequence by four residues. Polypeptide ChPepz was reported to hydrolyze an α-chymotrypsin substrate, whereas polypeptide TrPepz was said to hydrolyze a trypsin substrate. Subsequent workers were unable to reproduce the results reported by Atassi et al. See, Matthews et al., *Proc. Natl. Acad. Sci., USA*, 91:4103–4105 (1994); Corey et al., Ibid., 4106–4109; Wells et al., Ibid., 4110–4114.

An earlier report of Hahn et al., *Science*, 248:1544–1549 (1990) reported the synthesis and activity of a synthetic protein-like molecule named chymohelizyme-1 (CCHZ-1) composed of four parallel amphiphathic polypeptides covalently linked at their C-termini. Those four chains contained 17, 19, 21 and 15 residues. Molecule CHZ-1 also contained the α-chymotrypsin Ser/His/Asp catalytic triad, an oxyanion hole and a substrate binding pocket for acetyl-tryosine ethyl ester, an exemplary α-chymotrypsin substrate. This difficultly synthesized molecule was reported to exhibit affinity for α-chymotrypsin substrates and hydrolysis rates of about 0.01 that of the natural enzyme. More than 100 turnovers of the synthetic catalyst were reported.

Melittin is a 26-amino acid residue polypeptide that is the principal protein component of bee venom. Melittin has the amino acid sequence GlyIleGlyAlaValLeuLysValLeuThrThrGlyLeuPro—
AlaLeuIleSerTrpIleLysArgLysArgGlnGln—NH$_2$
(SEQ ID NO:1).

Melittin forms monolayers at air/water interfaces, dramatically lowering the surface tension of the water, and integrates into and disrupts natural and synthetic lipid membranes, leading to lysis of cells such as leukocytes, erythrocytes, lysosomes and mitochondria.

X-ray crystal structure data from melittin form I and form II crystals indicate that four melittin molecules associate with each other. Those data also indicate that residues 1–10 form a straight α-helix as do residues 13–26, with the axes of the two helices forming an obtuse angle with each other of about 120°. Terwilliger et al., *Biophys. J.*, 37:353–361 (1982); Terwilliger et al., *J. Biol. Chem.*, 257:6010–6015 (1982). The two α-helices are joined by a so-called "hinge region" comprised of residues 11 and 12.

The self-assembled tetrameric molecules are arrayed in two pairs of two anti-parallel chains laid across each other. The uncharged C-termini of the crossed molecules are relatively near each other, whereas the charged N-termini of the crossed molecules are relatively further apart.

Melittin has also been shown to be unfolded at micromolar concentration, at low ionic strength, and at neutral pH values, whereas the tetrameric α-helical structure is adopted under conditions of relatively high ionic strength, at alkaline pH values (about pH 9) or at elevated polypeptide concentrations. These structural changes were determined using residue molar ellipticity values obtained by circular dichroism measurements at about 200–230 nm.

The present inventors and their co-workers have extensively studied melittin, and more particularly its deletion and substitution analogues. Those melittin analogues possess antimicrobial activity as well as hemolytic activity toward red blood cells (erythrocytes). See, Blondelle et al., *Biochem.*, 30:4671–4678 (1991); Blondelle et al., *Pept. Res.*, 4:12–18 (1991); Blondelle et al., in *Peptides. Proceedings of the Twelfth American Peptide Symposium*, (Smith et al., eds.) Escom, Leiden, pp. 433–434 (1992); and Blondelle et al. in *Innovation and Perspectives in Solid Phase Syntheses*, Epton ed., Intercept, Andover, pp. 121–127 (1992).

Blondelle et al., *Biochim. Biophys. Acta*, 1202:331–336 (1993) reported on the effects of replacing each residue except Trp-19 with a Trp residue on erythrocyte lysis (hemolysis). Those results indicated that Trp for Leu replacements at positions 9, 13 and 16 resulted in decreases in activity, whereas replacements of Gly-1, Lys-7, Thr-11, Gly-12, Pro-14, Ala-15, Lys-21 or Lys-23 provided significant increases in hemolytic activity. Those substitutions at positions Gly-1 and Lys-21 extended the α-helices at either terminus, whereas substitution of either Thr-11 or Gly-12 reduced the length of the linking or hinge region between the two helical chains, and replacement of Pro-14 replaced a helix-disrupting residue with a helix-extender. The increases in hemolytic activity were generally well correlated to increases in helical character as measured by residue molar ellipticities and retention times on reversed phase high performance liquid chromatograph (RP-HPLC) using a C$_{18}$-column.

In a more recent study, Perez-Paya et al., *BioChem J.,* 299:587–591 (1994), a series of single residue substitution and omission melittin analogues were studied. These studies indicated that amphipathicity (amphiphilicity) as well as interchain distances and the orientation of hydrophobic residues were involved in the induction of stabilized tetrameric structures.

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.,* 85:2149–2154 (1963). The "Merrifield method" has for the most part remained largely unchanged and is used in nearly all automated peptide synthesizers available today.

Although most peptides are synthesized with the Merrifield procedure using automated instruments, a recent advance in the solid phase method by R. A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, *Proc. Natl. Acad. Sci.,* 82:5131–5135 (1985); Houghten et al., *Int. J. Peptide Protein Res.,* 27:673–678 (1986); and Houghten et al., Biotechniques, 4(6):522–528 (1986), whose disclosures are incorporated by reference.

Illustratively, the SMPS process employs porous containers such as plastic mesh bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

The interest in obtaining biologically active peptides for pharmaceutical, diagnostic and other uses would make desirable a procedure designed to find a mixture of peptides or a single peptide within a mixture with optimal activity for a target application. Screening mixtures of peptides enables the researcher to greatly simplify the search for useful therapeutic or diagnostic peptide compounds. Mixtures containing hundreds of thousands or more peptides are readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds because most are commonly present, and active, at nanomolar and lower concentrations. These compounds are also, in most instances, produced distant from their affection sites.

That a small peptide (or other molecule) can readily "find" an acceptor system, bind to it, and affect a necessary biological function prior to being cleared from the circulation or degraded suggests that a single specific peptide sequence can be present in a very wide diversity, and concentration, of other individual peptides and still be recognized by its particular acceptor system (antibody, cellular receptor, substrate, or the like). If one could devise a means to prepare and screen a large library of peptides containing up to milions of different sequences, the normal exquisite selectivity of biological affector/acceptor or other systems could be used to screen through vast numbers of synthetic oligopeptides.

Of interest in screening very large numbers of peptides is work by Geysen et al., which deals with methods for synthesizing peptides with specific sequences of amino acids and then using those peptides to identify reactions with various receptors. See U.S. Pat. Nos. 4,708,871, 4,833,092 and 5,194,392; P.C.T. Publications Nos. WO 84/03506 and WO 84/03564; Geysen et al., *Proc. Natl. Acad. Sci. U.S.A.,* 81:3998–4002 (1984); Geysen et al., *Proc. Natl. Acad. Sci. U.S.A.,* 82:178–182 (1985); Geysen et al., in *Synthetic Peptides as Antigens,* 130–149 (1986); Geysen et al., *J. Immunol. Meth.,* 102:259–274 (1987); and Schoofs et al., *J. Immunol.,* 140:611–616 (1988).

In U.S. Pat. No. 5,194,392, Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule. The mimotopes are prepared on a series of plastic rods.

The above method, although elegant, suffers from several disadvantages as to peptides. First, owing to the small size of each rod used, a relatively small amount of each peptide is produced. Second, each assay is carried out using the rod-linked peptides, rather than the free peptides in solution. Third, even though specific amounts of each blocked amino acid are used to prepare the mixed amino acid residues at the desired positions, there is no way of ascertaining that an equimolar amount of each residue is truly present at those positions.

Rutter et al. U.S. Pat. No. 5,010,175 discloses the preparation of peptide mixtures that are said to contain equimolar amounts of each reacted amino acid at predetermined positions of the peptide chain. Those mixtures are also said to contain each peptide in retrievable and analyzable amounts and are constructed by reacting mixtures of activated amino acids in concentrations based on the relative coupling constants of those activated amino acids.

In addition, Furka et al., (1988, 14th International Congress of Biochemistry, Volume 5, Abstract FR:013) and (1988, Xth International Symposium on Medicinal Chemistry, Budapest, Abstract 288, p. 168) described the synthesis of nine tetrapeptides each of which contained a single residue at each of the amino- and carboxy-termini and mixtures of three residues at each position therebetween. These mixture positions were obtained by physically mixing resins reacted with single amino acids. The abstract further asserts that those authors' experiments indicated that a mixture containing up to 180 pentapeptides could be easily synthesized in a single run. No biological or other activity assays were reported. More recently, Furka et al., *Int. J. Peptide Protein Res.*, 37:487–493 (1991) reported on the synthesis of mixtures of 27 tetrapeptides and 180 pentapeptides prepared by physically mixing reacted resin-linked peptides. Those peptides were synthesized with one or mixtures of three or four residues at each position along the chain. No biological or other activity results using those relatively simple mixtures were reported.

More recently still, Huebner et al. U.S. Pat. No. 5,182,366 described a similar process. Huebner et al. data provided for a mixture of tetramers having a glycine at position 2 from the amino- (N-) terminus and each of five different amino acid residues at positions 1, 3 and 4 from the N-terminus indicated that each of the residues at positions 1, 3 and 4 were present in substantially equimolar amounts and that glycine was present in its predicted amount. Similar data were also provided for twenty-five groups of pentamers, each of which had two known residues at the amino-termini and mixtures of five residues each at the remaining positions. No data were presented as to any activity or actually obtaining any selected peptide from the prepared mixtures.

A similar approach was also reported by Lam et al., *Letters to Nature*, 354:82–84 (1991). Those workers reported the preparation of millions of bead-linked peptides, each bead being said to contain a single peptide. The peptide-linked beads were reacted with a fluorescent- or enzyme-labeled acceptor. The beads bound by the acceptor were noted by the label and were physically removed. The sequence of the bound peptide was analyzed.

Recent reports (Devlin et al., *Science*, 249:404–405 [1990] and Scott et al., *Science*, 249:386–390 [1990]) have described the use of recombinant DNA and bacterial expression to create highly complex mixtures of peptides. More recently, Fodor et al., *Science*, 251:767–773 (1991), described the solid phase synthesis of thousands of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, Fodor et al. reported preparation of an array of 1024 different peptides coupled to the slide in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a combinatorial library is the inability of the peptides generated in those systems to interact in a "normal" manner with acceptor or substrate sites, analogous to natural interaction processes (i.e., free in solution at a concentration relevant to the receptors, antibody binding sites, enzyme binding pockets, reactant substrates or the like being studied without the exclusion of a large percentage of the possible combinatorial library), as well as the difficulties inherent in locating one or more active peptides. Secondarily, the expression vector systems do not readily permit the incorporation of the D-forms of the natural amino acids or the wide variety of unnatural amine acids which would be of interest in the study or development of such interactions.

Houghten et al., *Letters to Nature*, 354:84–86 (1991) reported use of physical mixtures in a somewhat different approach from those of Furka et al., Huebner et al. and Lam et al., supra, by using solutions of free, rather than support-coupled, peptide libraries or sets that overcomes several of the problems inherent in the above art. Here, 324 exemplary hexamer mixtures that contained more than 34 million peptides were first prepared whose N-terminal two positions were predetermined residues, whereas the C-terminal positions of the sets were equimolar amounts of eighteen of the twenty natural (gene-coded) L-amino acid residues. Binding studies were carried out using those 324 mixtures to determine which few provided optimal binding to a chosen receptor such as a monoclonal antibody or live bacterial cells. That study determined the two N-terminal optimal binding residues.

Another eighteen sets were then prepared keeping the optimal first two optimal binding residues, varying the third position among the eighteen L-amino acids used, and keeping the C-terminal three positions as equimolar mixtures. Binding studies were again carried out and an optimal third position residue was determined. This general procedure was repeated until the entire hexamer sequence was determined.

Similar studies are also reported in Pinilla et al. *Vaccines 92*, Cold Spring Harbor Laboratory Press, Cold Spring Harbor, pages 25–27 (1992); Appel et al., *Immunomethods*, 1:17–23 (1992); Houghten et al., *BioTechniques*, 13:412–421 (1992); Houghten et al., in *Innovation and Perspectives in Solid Phase Syntheses: Peptides, Polypeptides and Oligonucleotides*, R. Epton (ed.), Intercept, Ltd., Andover, pages 237–239 (1992); Houghten et al., in *Peptides*, J. A. Smith and J. E. Rivier (eds.), Proceedings of the Twelfth American Peptide Symposium, ESCOM, Leiden, pages 560–561 (1992); and WO 92/09300 published Jun. 11, 1992.

A still different approach was reported in Pinilla et al., *BioTechniques*, 13:901–905 (1992). In that report, a total of 108 free hexamer peptide mixture sets were prepared. Those sets contained one of eighteen amino acid residues at each of the six positions of the hexamer chains, with the other five positions being occupied by equimolar amounts of those same eighteen residues. Again, over 34 million different peptides were represented by those 108 sets (6 positions×18 residues/position).

Each of the sets was assayed for binding to a monoclonal antibody as receptor. The residue at each position that provided best binding results for that position provided a peptide sequence that was identical to the known epitope for that monoclonal. This process also provided sequences for other peptides that were bound almost as well by the monoclonal.

The peptide sets or libraries reported to date have themselves been ligands that bind to an acceptor (receptor), but once bound, carry out no reaction. It would thus be beneficial if the above peptide library approach could be expanded to encompass materials that possess an activity of their own so that an inherent property could be optimized, or a previously non-existent or minimal activity could be created or enhanced. The disclosure that follows relates to such a system that provides catalytic activity to a relatively short polypeptide.

BRIEF SUMMARY OF THE INVENTION

The present invention relates to analogues of melittin and to sets and sets of sets (libraries) of melittin analogue polypeptides that exhibit one or more types of hydrolytic catalysis, as well as to the use of such sets and libraries to determine an optimal melittin analogue sequence for catalyzing a particular hydrolytic reaction in a predetermined substrate molecule.

One aspect of the invention contemplates a set of polypeptides that comprises a mixture of equimolar amounts of polypeptide chain members having the sequence $$Xaa^1Xaa^2Xaa^3GlyIleGlyAlaValLeuXaa^{10}ValLeu-$$
$$Xaa^{13}Xaa^{14}Xaa^{15}Xaa^{16}Xaa^{17}AlaLeuIleSer-$$
$$TrpIleLysArgXaa^{26}Xaa^{27}Xaa^{28}Xaa^{29}$$
(SEQ ID NO:2)

For each polypeptide (a) each of $Xaa^1$, $Xaa^2$ and $Xaa^3$ is present or absent, but $Xaa^2$ is present only if $Xaa^3$ is present, and $Xaa^1$ is present only if $Xaa^2$ is present;

(b) $Xaa^3$, when present, is an amino acid residue selected from the group consisting of Asp, Glu, Asn, Gln, Ser, Lys and Arg;

(c) $Xaa^2$, when present, is an amino acid residue selected from the group consisting of Asp, Glu, Asn, Gln, Ser, Lys and Arg;

(d) $Xaa^1$, when present, is an amino acid residue selected from the group consisting of Ala, Val, Leu, Ile, Trp and Phe;

(e) $Xaa^{10}$ is an amino acid residue selected from the group consisting of Lys, Asp and Glu;

(f) $Xaa^{26}$, $Xaa^{27}$, $Xaa^{28}$ and $Xaa^{29}$ are present or absent, but $Xaa^{27}$ is present only if $Xaa^{26}$ is present, $Xaa^{28}$ is present only if $Xaa^{27}$ is present, and $Xaa^{29}$ is present only if $Xaa^{28}$ is present;

(g) $Xaa^{26}$, when present, is Lys, $Xaa^{27}$, when present, is Arg, $Xaa^{28}$, when present, is Gln and $Xaa^{29}$, when present, is Gln—$NH_2$; and (h) each of $Xaa^{13}$, $Xaa^{14}$, $Xaa^{15}$, $Xaa^{16}$ and $Xaa^{17}$ is one of at least six different predetermined amino acid residues.

And, for the polypeptide set (a') at least one of $Xaa^{13}$, $Xaa^{14}$, $Xaa^{15}$, $Xaa^{16}$ and $Xaa^{17}$ is the same, predetermined residue, present at the same chain position in each polypeptide; and (b') at least one other chain position occupied by $Xaa^{13}$, $Xaa^{14}$, $Xaa^{15}$, $Xaa^{16}$ and $Xaa^{17}$ contains an equimolar amount of those at least six different amino acid residues.

In more preferred practice, a set of polypeptides is contemplated that comprises a mixture of equimolar amounts of polypeptide chain members having the sequence $$GlyIleGlyAlaValLeuXaa^7ValLeuXaa^{10}Xaa^{11}Xaa^{12}-$$
$$Xaa^{13}Xaa^{14}AlaleuIleSerTrpIle-$$
$$LysArgLysArgGlnXaa^{26}$$
(SEQ ID NO:3)

For each polypeptide (a) $Xaa^7$ is an amino acid residue selected from the group consisting of Lys, Asp and Glu;

(b) each of $Xaa_{10}$, $Xaa^{11}$, $Xaa^{12}$, $Xaa^{13}$ and $Xaa^{14}$ is one of at least six amino acids; and (c) $Xaa^{26}$ is Gln—$NH_2$.

And, for a polypeptide set (a') at least one of $Xaa^{10}$, $Xaa^{11}$, $Xaa^{12}$, $Xaa^{13}$ and $Xaa^{14}$ is the same predetermined residue, present at the same chain position in each polypeptide; and (b') at least one other chain position occupied by $Xaa^{10}$, $Xaa^{11}$, $Xaa^{12}$, $Xaa^{13}$ and $Xaa^{14}$ contains an equimolar amount of said at least six different amino acid residues.

An iterative process for determining the sequence of a linear polypeptide that exhibits enhanced or preferential antimicrobial, hemolytic activity or catalytic hydrolysis of a predetermined substrate is also contemplated. That process comprises the steps of:

(i) providing a library of a plurality of sets of linear polypeptides in which each set comprises a mixture of equimolar amounts of polypeptide member chains having the sequence $$Xaa^1Xaa^2Xaa^3GlyIleGlyAlaValLeuXaa^{10}ValLeu-$$
$$Xaa^{13}Xaa^{14}Xaa^{15}Xaa^{16}Xaa^{17}AlaLeuIleSer-$$
$$TrpIleLysArgXaa^{26}Xaa^{27}Xaa^{28}Xaa^{29}$$
(SEQ ID NO:2)

For each polypeptide (a) each of $Xaa^1$, $Xaa^2$ and $Xaa^3$ is present or absent, with the provisos that $Xaa^2$ is present only if $Xaa^3$ is present, and $Xaa^1$ is present only if $Xaa^2$ is present;

(b) $Xaa^3$ when present is an amino acid residue selected from the group consisting of Asp, Glu, Asn, Gln, Ser, Lys and Arg;

(c) $Xaa^2$ when present is an amino acid residue selected from the group consisting of Asp, Glu, Asn, Gln, Ser, Lys and Arg;

(d) $Xaa^1$ when present is an amino acid residue selected from the group consisting of Ala, Val, Leu, Ile, Trp and Phe;

(e) $Xaa^{10}$ is an amino acid residue selected from the group consisting of Lys, Asp and Glu;

(f) $Xaa^{26}$, $Xaa^{27}$, $Xaa^{28}$ and $Xaa^{29}$ are present or absent, with the provisos that $Xaa^{27}$ is present only if $Xaa^{26}$ is present, $Xaa^{28}$ is present only if $Xaa^{27}$ is present, and $Xaa^{29}$ is present only if $Xaa^{28}$ is present;

(g) $Xaa^{26}$ when present is Lys, $Xaa^{27}$ when present is Arg, $Xaa^{28}$ when present is Gln and $Xaa^{29}$ when present is Gln—$NH_2$; and (h) each of $Xaa^{13}$, $Xaa^{14}$, $Xaa^{15}$, $Xaa^{16}$ and $Xaa^{17}$ is one of at least six different predetermined amino acid residues.

For each polypeptide set:

(a') one or more of $Xaa^{13}$, $Xaa^{14}$, $Xaa^{15}$, $Xaa^{16}$ and $Xaa^{17}$ is the same, predetermined residue, present at the same one or more chain positions in each polypeptide; and (b') at least one other chain position is occupied by $Xaa^{13}$, $Xaa^{14}$, $Xaa^{15}$, $Xaa^{16}$ and $Xaa^{17}$ contains an equimolar amount of those at least six different amino acid residues.

Each set of that library differs from the other sets in the identity of the one or more same predetermined residues present at the same one or more predetermined chain position within each set.

(ii) Each set from that library of sets is separately admixed with microbes, red blood cells or catalyst substrate in an aqueous medium at a set concentration of about 0.1 milligrams per liter to about 100 grams per liter. The activity exhibited by each set is separately assayed, and a set exhibiting preferential antimicrobial, hemolytic or catalytic activity, respectively, relative to the other sets is determined, thereby identifying one or more amino acid residues that provided preferential activity at the one or more predetermined positions.

(iii) A second library of sets is provided that is identical to the first-named library of sets except for the polypeptide sequences at $Xaa^{13-17}$. The second library of sets contains the one or more amino acid residues of the first-named library identified as exhibiting preferential activity in the same one or more predetermined chain positions as in the sets of the first-named library. The member polypeptide chains of the sets of the second library have a predetermined one of those same at least six different amino acid residues at another predetermined position within chain positions $Xaa^{13-17}$ different from the one or more positions of the identified one or more amino acid residues of the first-named library of sets. Each of the second library of sets has equimolar amounts of the at least six different amino acid residues of the first-named library of sets at the same one or more positions of the polypeptide chain positions $Xaa^{13-17}$ not occupied by the one or more identified amino acid residues or the predetermined amino acid residues, and has one fewer polypeptide positions occupied by equimolar amounts of at least six different amino acid residues than the first-named library of sets.

(iv) Each set of the second library of sets is separately admixed with microbes, red blood cells or substrate in an aqueous medium at a set concentration of about 0.1 milligrams per liter to about 100 grams per liter. The antimicrobial, hemolytic or catalytic activity, respectively, exhibited by each set is separately assayed. A second set exhibiting preferential activity relative to the other second library sets is determined, thereby identifying an amino acid residue that provides preferential activity at the other predetermined position in the polypeptide chain.

(v) Steps (iii) and (iv) are repeated using zero through two further libraries of sets of linear polypeptides instead of the second library of sets or until preferential activity does not increase when a further library is assayed. Each further library of sets of linear polypeptides comprises a mixture of equimolar amounts of member linear polypeptide chains containing the same polypeptide sequence except for positions $Xaa^{13-17}$ as utilized in the first-named library of sets. The member chains of the sets of each further library contain the amino acid residues in the polypeptide chain positions $Xaa^{13-17}$ that exhibited preferential activity such as catalytic hydrolysis in a library of sets used immediately before, and a predetermined one of the at least six different amino acid residues at another predetermined position within $Xaa^{13-17}$ of the polypeptide chain different from the positions of the identified amino acid residues of the library of sets used immediately before. Each of the further libraries of sets has equimolar amounts of the at least six different amino acid residues of the first-named sets at the same one or more positions $Xaa^{13-17}$ of the polypeptide chain not occupied by the identified amino acid residues or the predetermined amino acid residues.

(vi) Where the last-assayed library of sets exhibits increased preferential antimicrobial, hemolytic or catalytic activity compared to the library used immediately before and one position of the polypeptide chain that provides preferential activity is not identified, at least six polypeptide chains are provided in which each chain contains the same polypeptide sequence except for positions $Xaa^{13-17}$ as utilized in the first-named libraries of sets. Each polypeptide chain contains the identified amino acid residues in the polypeptide chain positions that exhibited increased preferential activity in the immediately preceding assay of step (v) and a predetermined one of the at least six different amino acid residues at another predetermined position in the polypeptide chain different from the positions of the identified amino acid residues used in the immediately preceding assay of step (v).

(vii) Each of the at least six polypeptides of setp (vi) is separately admixed with microbes, red blood cells or catalyst substrate in an aqueous medium at a polypeptide concentration of about 0.1 milligrams to about 100 grams per liter. The antimicrobial, hemolytic or hydrolytic activity, respectively, exhibited by each polpeptide is separately assayed. The polypeptide exhibiting preferential activity is determined, thereby determining the sequence of a linear polypeptide that exhibits preferential antimicrobial, hemolytic or catalytic activity.

Another embodiment contemplates use of a somewhat different process for determining the sequence of a linear polypeptide that exhibits enhanced or preferenctial antibmicrobial, hemolytic or catalytic hydrolysis of a predetermined substrate. This process comprises the steps of:

(i) providing a library of a plurality of sets of linear polypeptides in which each set comprises a mixture of equimolar amounts of polypeptide member chains having the sequence $Xaa^1Xaa^2Xaa^3GlyIleGlyAlaValLeuXaa^{10}ValLeu—$
$Xaa^{13}Xaa^{14}Xaa^{15}Xaa^{16}Xaa^{17}AlaLeuIleSer—$
$TrpIleLysArgXaa^{26}Xaa^{27}Xaa^{28}Xaa^{29}$ (SEQ ID NO:2)

For each polypeptide
(a) each of $Xaa^1$, $Xaa^2$ and $Xaa^3$ is present or absent, with the provisos that $Xaa^2$ is present only if $Xaa^3$ is present, and $Xaa^1$ is present only if $Xaa^2$ is present;
(b) $Xaa^3$ when present is an amino acid residue selected from the group consisting of Asp, Glu, Asn, Gln, Ser, Lys and Arg;
(c) $Xaa^2$ when present is an amino acid residue selected from the group consisting of Asp, Glu, Asn, Gln, Ser, Lys and Arg;
(d) $Xaa^1$ when present is an amino acid residue selected from the group consisting of Ala, Val, Leu, Ile, Trp and Phe;
(e) $Xaa^{10}$ is an amino acid residue selected from the group consisting of Lys, Asp and Glu;
(f) $Xaa^{26}$, $Xaa^{27}$, $Xaa^{28}$ and $Xaa^{29}$ are present or absent, with the provisos that $Xaa^{27}$ is present only if $Xaa^{26}$ is present, $Xaa^{28}$ is present only if $Xaa^{27}$ is present, and $Xaa^{29}$ is present only if $Xaa^{28}$ is present;
(g) $Xaa^{26}$ when present is Lys, $Xaa^{27}$ when present is Arg, $Xaa^{28}$ when present is Gln and $Xaa^{29}$ when present is Gln—NH$_2$; and
(h) each of $Xaa^{13}$, $Xaa_{14}$, $Xaa^{15}$, $Xaa^{16}$ and $Xaa^{17}$ is one of at least six different predetermined amino acid residues.

For each polypeptide set
(a) one of $Xaa^{13}$, $Xaa^{14}$, $Xaa^{15}$, $Xaa^{16}$ and $Xaa^{17}$ is the same, predetermined residue, present at the same chain position in each polypeptide; and (b) at least one other chain position occupied by Xaa$^{13}$, Xaa$^{14}$, Xaa$^{15}$, Xaa$^{16}$ and Xaa$^{17}$ contains an equimolar amount of those at least six different amino acid residues.

Each set of that library differs from the other sets in the identity and chain position of the one same predetermined residue present at the same predetermined chain position within each set.

(ii) Each set from the library of sets is separately admixed with microbes, red blood cells or catalyst substrate in an aqueous medium at a set concentration of about 0.1 milligrams per liter to about 100 grams per liter. The antimicrobial, hemolytic or catalytic activity, respectively, exhibited by each set is separately assayed.

The residue that exhibited preferential activity at each of positions Xaa$^{13-17}$ provides the sequence of a polypeptide that preferentially catalyzes hydrolysis of said substrate.

The present invention has several benefits and advantages.

One benefit of the invention is that use of its process permits one to optimize a catlytic property in a melittin sequence.

An advantage of the invention is its relatively simple and straightforward technique used for optimization.

Still further benefits and advantages of the invention will be apparent to those skilled in the art from the discussion that follows.

Detailed Description of the Invention Introduction

Catalyst discovery involving polypeptides invariably requires the synthesis and testing of hundreds to thousands of analogues of an original active sequence. In order to understand a given molecule's structure activity relationships, very large numbers of polypeptide analogues are needed in all of these areas.

The diversity of the combinatorial possibilities of even the 20 natural amino acids makes usually-used synthesis methods sorely limited in the task of screening for optimal polypeptide catalysts, antigens, peptide ligands for biologically relevant or other acceptor systems, enzyme inhibitors, antimicrobials, and the like [i.e., there are 64,000,000 possible six residue peptides (20$^6$), 1,280,000,000 possible seven residue peptides (20$^7$), and the like] Although the usually-used methods for single polypeptide syntheses have greatly facilitated studies with synthetic polypeptides, and are available commercially either on a custom basis or for use in kit form, they permit only a very small fraction of possible polypeptides (composed of either natural or unnatural amino acids) to be prepared.

Equimolar amounts of each component making up the library (or member set) to be studied ensures the necessary selectivity of the interactions of the desired polypeptide in the mixture to be used (i.e., the "needle in the haystack"-finding the correct hexapeptide in the 64,000,000 possible combinations of the 20 natural amino acid residues would be analogous to finding a single steel needle in 63,999,999 copper needles). As an insight into the extreme selection criterion involved in such a system, it is helpful if one considers that a single six-letter word would have to be readily found in the presence of 63,999,999 other six-letter words (63,999,999 six-letter words would fill approximately 50,000 pages of text of the font size found in a usual scientific journal).

The present invention relates to sets of mixtures of melittin polypeptide analogues that have catalytic activity, as well as individual catalyst molecules. These molecules also have hemolytic activity that can similarly be optimized. A contemplated set of melittin analogue polypeptides preferably contains an acidic amino acid (Glu or Asp) in place of the lysine normally found at position 7 of the melittin sequence. Glutamic acid is the more preferred residue at position 7.

A contemplated set of melittin analogues also contains at least one mixture of equimolar amounts of at least six different amino acid residues at a predetermined position that can be any of positions 10, 11, 12, 13 or 14 of the melittin sequence (SEQ ID NO:3), as well as at least one predetermined residue of those same at least six different amino acid residues at another predetermined position of positions 10, 11, 12, 13 or 14 not occupied by the mixture of residues. Thus, at the extremes, a contemplated set can contain a mixture of those at least six different amino acid residues at four of positions 10–14 and a single residue of those six at the other position, or one position of positions 10–14 of such a mixture and the other four as four individual, predetermined residues.

Each set member has the same chain length and terminal groups. For the N-terminus, a free α-amino group is present, whereas for the C-terminus, a carboxamide [—C(O)NH$_2$] is present.

A polypeptide of a contemplated set or an individual polypeptide can include the naturally occurring 20 L-amino acids, one or both isomers of ornithine, norleucine, hydroxyproline, β-alanine and the other C$_3$–C$_7$ amino acids such as γ-aminobutyric and ε-aminocaproic acids and the D-stereoisomers of the naturally occurring twenty amino acids, as well as N-methyl and N-ethyl derivatives of those amino acids so that use of about 80–90 individual protected D- and L-amino acids is contemplated for synthesis and use at positions Xaa$^{13-17}$ or Xaa$^{10-14}$ as appropriate. Polypeptide sets that contain all D-amino acid residues and mixtures of both D- and L-forms are contemplated for use herein.

Consequently, as used herein, the term "amino acid" is, unless otherwise stated, intended to include not only the naturally occurring (RNA encoded) L-amino acids but also their D-stereoisomers and unnatural C$_3$–C$_7$ amino acids. The phrases "amino acid derivative", "protected amino acid derivative" or the like are used herein for a protected amino acid added as a reactant, whereas the phrase "amino acid residue", "residue" or the like is used herein for a reacted protected or deprotected amino acid that is a portion of a polypeptide chain.

All oligopeptide and polypeptide formulas or sequences shown herein are written from left to right and in the direction from amino-terminus to carboxy-terminus. The abbreviations used herein for derivatives and residues of the twenty natural amino acids are reproduced in the following Table of Correspondence:

| TABLE OF CORRESPONDENCE | | |
|---|---|---|
| Abbreviation | | |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |

TABLE OF CORRESPONDENCE

| Abbreviation | | |
|---|---|---|
| 1-Letter | 3-Letter | Amino Acid |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A melittin analogue or set thereof similarly contains a before-defined amino acid residue whose identity is known or specifically defined.

A "predetermined position" in a polypeptide mixture sequence or chain is a position, from and including the amino-terminal residue as position 1, occupied by a predetermined amino acid residue or of a mixture of residues, and which position is known and specifically identified. Position numbering on a contemplated polypeptide or set of polypeptides is taken from the first (N-terminal) glycine in naturally occurring melittin and continue toward the C-terminus. Where an additional residue is present upstream from the natural, N-terminal Gly, the molecule is renumbered from the new N-terminal residue as position 1.

The letter "O" is used herein to indicate a predetermined, but unspecified single amino acid residue of a polypeptide. Subscripted letters "O", e.g., $O_1, O_2, O_3 \ldots O_n$ etc. indicate a predetermined amino acid residue that is predetermined (specified) and at the same position $(1, 2, 3 \ldots n)$ among a set of polypeptide mixtures, solid support-coupled polypeptide mixture set, that is free or solid support-coupled. Thus, a subscripted letter "O" such as $O_1$ is used where a particular amino acid residue is intended such as alanine or leucine, whereas an unsubscripted letter "O" is used to mean that each of the plurality of residues is present at a given position, but that that residue is not specified, yet is a single residue. Subscripted numbers start at the amino-terminus for any given mixture.

The letter "X" is used to indicate that a position in an polypeptide set formula occupied by that letter is an equimolar mixture of each of at least six amino acid residues, and preferably ten or more such residues, and more preferably about 15 to about 20.

The letter "B" is used to indicate a solid support used in the syntheses described herein, such as a particulate resin.

As used herein, the word "polypeptide" is applied to chains containing more than 10 amino acid residues, whereas the word "oligopeptide" is applied to chains containing fewer than 10 amino acid residues. The word "peptide" is used generically to mean a chain of any length that is composed of amino acid residues.

Polypeptide Sets

As already noted, the present invention contemplates a set of polypeptide mixtures, libraries of such sets, and also individual polypeptide molecules. A contemplated set of polypeptides comprises a mixture of equimolar amounts of polypeptide chain members, each having the sequence

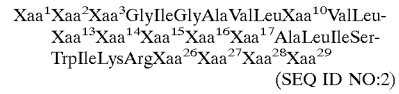

$Xaa^1Xaa^2Xaa^3$GlyIleGlyAlaValLeu$Xaa^{10}$ValLeu-$Xaa^{13}Xaa^{14}Xaa^{15}Xaa^{16}Xaa^{17}$AlaLeuIleSer-TrpIleLysArg$Xaa^{26}Xaa^{27}Xaa^{28}Xaa^{29}$ (SEQ ID NO:2)

wherein for a peptide
(a) each of $Xaa^1$, $Xaa^2$ and $Xaa^3$ is present or absent, but $Xaa^2$ is present only if $Xaa^3$ is present, and $Xaa^1$ is present only if $Xaa^2$ is present;
(b) $Xaa^3$, when present, is an amino acid residue selected from the group consisting of Asp, Glu, Asn, Gln, Ser, Lys and Arg;
(c) $Xaa^2$, when present, is an amino acid residue selected from the group consisting of Asp, Glu, Asn, Gln, Ser, Lys and Arg;
(d) $Xaa^1$, when present, is an amino acid residue selected from the group consisting of Ala, Val, Leu, Ile, Trp and Phe;
(e) $Xaa^{10}$ is an amino acid residue selected from the group consisting of Lys, Asp and Glu;
(f) $Xaa^{26}$, $Xaa^{27}$, $Xaa^{28}$ and $Xaa^{29}$ are present or absent, but $Xaa^{27}$ is present only if $Xaa^{26}$ is present, $Xaa^{28}$ is present only if $Xaa^{27}$ is present, and $Xaa^{29}$ is present only if $Xaa^{28}$ is present; and
(g) $Xaa^{26}$, when present, is Lys, $Xaa^{27}$, when present, is Arg, $Xaa^{28}$, when present, is Gln and $Xaa^{29}$, when present, is Gln—$NH_2$; and
(h) each of $Xaa^{13}$, $Xaa^{14}$, $Xaa^{15}$, $Xaa^{16}$ and $Xaa^{17}$ is one of at least six different predetermined amino acid residues; and wherein for the set
(a') at least one of $Xaa^{13}$, $Xaa^{14}$, $Xaa^{15}$, $Xaa^{16}$ and $Xaa^{17}$ is the same, predetermined residue, present at the same chain position in each polypeptide; and
(b') at least one other chain position occupied by $Xaa^{13}$, $Xaa^{14}$, $Xaa^{15}$, $Xaa^{16}$ and $Xaa^{17}$ contains an equimolar amount of those at least six different amino acid residues.

In preferred practice, $Xaa^3$ is absent so that $Xaa^1$ and $Xaa^2$ are also absent. It is also preferred that $Xaa^{29}$ also be present so that $Xaa^{26}$, $Xaa^{27}$ and $Xaa^{28}$ are also present.

As a consequence, a most preferred set of polypeptides comprises a mixture of equimolar amounts of polypeptide chain members, each having the sequence

GlyIleGlyAlaValLeu$Xaa^7$ValLeu$Xaa^{10}Xaa^{11}Xaa^{12}$—$Xaa^{13}Xaa^{14}$AlaLeuIleSerTrpIle—LysArgLysArgGln$Xaa^{26}$ (SEQ ID NO:3)

wherein for a polypeptide
(a) $Xaa^7$ is an amino acid residue selected from the group consisting of Lys, Asp and Glu;
(b) each of $Xaa^{10}$, $Xaa^{11}$, $Xaa^{12}$, $Xaa^{13}$ and $Xaa^{14}$ is one of at least six amino acids; and (c) $Xaa^{26}$ is Gln—$NH_2$; and
wherein for said set
(a') at least one of $Xaa^{10}$, $Xaa^{11}$, $Xaa^{12}$, $Xaa^{13}$ and $Xaa^{14}$ is the same predetermined residue, present at the same chain position in each polypeptide; and
(b') at least one other chain position occupied by $Xaa^{10}$, $Xaa^{11}$, $Xaa^{12}$, $Xaa^{13}$ and $Xaa^{14}$ contains an equimolar amount of those at least six different amino acid residues.

In each of the polypeptides contemplated, it is more preferred that $Xaa^{10}$ of SEQ ID NO:2 and $Xaa^{7}$ of SEQ ID NO:3 be either Asp or Glu, with Glu being most preferred. Both of the acidic residues form more stable tetramers than when the residue is Lys, as in melittin.

Turning to a peptide of SEQ ID NO:2, the addition of each of $Xaa^{3}$, $Xaa^{2}$ and $Xaa^{1}$ ($Xaa^{1-3}$) extends the amphiphathic α-helix toward the N-terminus of the polypeptide chain. Thus, the residues of $Xaa^{3}$ and $Xaa^{2}$ are hydrophilic, whereas an added $Xaa^{1}$ residue is a hydrophobic residue. These additions are to the shorter α-helix of the melittin polypeptide, and based on crystal structure data do not interfere with tetramer formation.

For $Xaa^{1-3}$, it is noted that if $Xaa^{3}$ is absent, so are $Xaa^{2}$ and $Xaa^{1}$. Similarly, if $Xaa^{3}$ is present, $Xaa^{2}$ can also be present as can $Xaa^{1}$. Likewise, only when both $Xaa^{3}$ and $Xaa^{2}$ are present, can $Xaa^{1}$ also be present.

Hemolytic studies indicate that the four C-terminal residues can be deleted with little loss in activity. Blondelle et al., in *Innovation and Perspectives in Solid Phase Syntheses*, Epton ed., Intercept, Andover (1992) pp. 121–127. Thus, each of the specific residues of $Xaa^{26}$, $Xaa^{27}$, $Xaa^{28}$ and $Xaa^{29}$ ($Xaa^{26-29}$) of SEQ ID NO:2 can be omitted, as can groups of those residues. These omissions shorten the longer α-helix of the melittin polypeptide.

The presence or absence of each of $Xaa^{26-29}$ is similarly dependent upon the presence of a preceding $Xaa^{26-29}$ residue. Thus, $Xaa^{29}$ is only present when $Xaa^{28}$ is also present, and $Xaa^{28}$ is only present when $Xaa^{27}$ is also present, and so on.

As noted before, use of about 80–90 different amino acid residues is contemplated here. Those residues are the naturally occurring (RNA encoded) L-amino acid residues, as well as their corresponding D-amino acid residues. Also contemplated are $C_3$–$C_7$ amino acids such as 2-aminoadipic acid (Aad), 3-aminoadipic acid (bAad), β-alanine (bAla), 2-aminobutyric aid (Abu), 4-aminobutyric acid (4Abu), 6-aminocaproic acid (Acp), 2-aminoheptanoic acid (Ahe), 2-aminoisobutyric acid (Aib), 3-aminoisobutyric acid (bAib), 2-aminopimelic acid (Apm), 2,4-diaminobutyric acid (Dbu), desmosine (Des), 2,2'-diaminopimetic acid (Dpm), 2,3-diaminopropionic acid (Dpr), N-ethylglycine (EtGly), N-ethylasparagine (EtAsn), hydroxylysine (Hyl), allo-hydroxylysine (aHyl), 3-hydroxyproline (3Hyp), 4-hydroxyproline, isodesmosine (Ide), allo-isoleucine (alle), sarcosine (MeGly), N-methylisoleucine (MeIle), N-methylvaline (MeLys), norvaline (Nva), norleucine (Nle), ornithine (Orn), and penicillamine. Use of both D- and L-isomers, where such exist, is contemplated.

Use of the 20 naturally occurring L-amino acid residues is preferred herein for positions $Xaa^{13-17}$ of SEQ ID NO:2 or $Xaa^{10-14}$ of SEQ ID NO:3. More preferred is the use of all of those residues except cysteine. Although use of those naturally occurring 19 L-residues is most preferred, the present invention can be practiced with the L-amino acid residues enumerated in the sequence, along with at least six, preferably about 10 to about 15, and more preferably at least 19 residues that include all, some or none of the residues enumerated in a sequence.

Thus, each of $Xaa^{13-17}$ of SEQ ID NO:2 and $Xaa^{10-14}$ of SEQ ID NO:3 is one of at least six predetermined amino acid residues, preferably about 10 to about 15 residues, and more preferably at least 19 residues. The $Xaa^{13-17}$ and $Xaa^{10-14}$ residues are selected from a group of known residues. However, when present in a mixture set, except at one position, the identity of an individual residue at a particular position can be difficult to determine because of the complexity of the mixture.

As to that exception, at least one; i.e., one or more, of $Xaa^{13-17}$ and $Xaa^{10-14}$ is the same, predetermined residue present at the same polypeptide chain position in each polypeptide member chain of the set. Thus, should it be desired that Ala be the predetermined residue at chain position $Xaa^{11}$, all of the chains of that set have an Ala at chain position $Xaa^{11}$. More than one position, but not all of $Xaa^{13-17}$ or $Xaa^{10-14}$ can be predetermined with the same or a different, single predetermined residue of the at least six different amino acid residues used. Thus, for example, $Xaa^{11}$ could be Ala, $Xaa^{12}$ Trp, $Xaa^{13}$ Gly and $Xaa^{10}$ Lys.

Within the set, at least one other chain position of the $Xaa^{13-17}$ and $Xaa^{10-14}$; i.e., one polypeptide chain position other than that having the at least one same predetermined residue, contains an equimolar amount of those at least six different amino acid residues. Thus, up to four of positions $Xaa^{13-17}$ and $Xaa^{10-14}$ can contain equimolar amounts of the at least six amino acid residues used in a set.

As will be discussed hereinafter, it is particularly preferred in one embodiment that a set contain polypeptides in which only one position of $Xaa^{13-17}$ and $Xaa^{10-14}$ is occupied by a single, known, predetermined residue with the other four of those positions containing equimolar amounts of those at least six different amino acid residues.

To recapitulate, a contemplated set of polypeptide chains contains a core sequence of the two α-helices of melittin (or an Asp or Glu exchanged residue for $Lys^{-7}$ of melittin) linked together by an expanded hinge region; i.e., positions $Xaa^{10-14}$ of SEQ ID NO:3, of varying sequence. Within that expanded hinge region, at least one position has the same one of at least six different, known, predetermined residue for all of the polypeptides of the set, and at least one position is occupied by an equimolar amount of those some at least six different residues.

Further exemplary sets contain polypeptide chains that can be defined by reference to the residue positions of a polypeptide of SEQ ID NO:2, while maintaining the position numbers of that sequence. Thus, for example, the polypeptides of one exemplary set have the sequence of a polypeptide of SEQ ID NO:2 from position 2 through 29, whereas another has that sequence from position 3 through 29 and a third has the sequence of position 4 through 29; i.e., SEQ ID NO:3. The polypeptides of another set have the sequence of a polypeptide of SEQ ID NO:2 from position 1 through 28, whereas another has a sequence of positions 2 through 27, a third positions 3 through 27, a fourth positions 4 through 25, and so on.

More generally, a polypeptide of a contemplated set can contain 22 amino acid residues; i.e., $Xaa^{1-3}$ and $Xaa^{26-29}$ absent=22 residues, through the 29 residues of SEQ ID NO:2, with all residues present. There are about twenty different combinations of sequence and length that can be utilized to provide a set of polypeptides having the above length requirement. Each of those about 20 combinations is contemplated, with the combination of SEQ ID NO:3 being particularly preferred.

Sets of sets or libraries are also contemplated. Within any library, the sequence of the polypeptide set members on either side of $Xaa^{13-17}$ and $Xaa^{10-14}$ of SEQ ID NO's:2 and 3, respectively, are the same. In an exemplary library whose sets have one predetermined residue and four equimolar mixture positions, the sets differ only in the identity of the individual six different known, predetermined residues at the same sequence position. Six sets thus define this library. For example, where Ala, Gly, Asp, Lys, Gln and Trp are the six different residues, and position $Xaa^{10}$ of SEQ ID NO:3 is the position of the known, predetermined residue, the six sets have Ala, Gly, Asp, Lys, Gln and Trp, respectively, at position $Xaa^{10}$ and equimolar amounts of those residues at the remaining four positions.

Another exemplary library is composed of another similar six sets having polypeptides with one each of the above residues at position $Xaa^{11}$, with the sets having equimolar amounts of those same six residues at the other four variable hinge positions. It should be apparent that three similar libraries can be prepared by utilizing each of the above six residues at each of polypeptide positions $Xaa^{12}$, $Xaa^{13}$ and $Xaa^{14}$ in those separate libraries, with the other positions of $Xaa^{10-14}$ being occupied by equimolar amounts of those residues. Thus, five libraries of six sets each, or 30 sets are defined.

Where the preferred about 10 to about 15 known, predetermined residues are utilized, five libraries of about 10 to about 15 sets are defined. Where the most preferred 19 L-amino acid residues are used, 95 sets are defined.

Another exemplary library contains sets in which the polypeptides have two known residues at two preferably adjacent positions, e.g. at $Xaa^{10}$ and $Xaa^{11}$, and the sets have equimolar mixtures at the other three chain positions. Where six different residues are used at the predetermined, known and mixture positions, the library contains 36 (6×6) sets, whereas where 20 residues are used, the library contains 400 (20×20) sets.

A related library contains sets whose polypeptides have single, predetermined, known residues at positions $Xaa^{10}$ and $Xaa^{11}$, e.g. $O_{10-a}$ and $O_{11-b}$, each of the at least six residues at position $Xaa^{12}$ ($O_{12}$) and mixtures at positions $Xaa^{13}$ and $Xaa^{14}$ ($X_{13}$ and $X_{14}$). Where 20 amino acid residues are used as above, another 20 libraries are defined.

Another related library contains sets whose polypeptides have the same, single, predetermined known residues at positions $Xaa^{10}$, $Xaa^{11}$ and $Xaa^{12}$, e.g., $O_{10-a}O_{11-b}O_{12-c}$, one each of the at least six different residues at position $Xaa^{13}$ ($O_{13}$) and an equimolar mixture of residues at position $Xaa^{14}$ ($X_{14}$). A further group of 20 sets are within this library when 20 amino acid residues are used at positions $Xaa^{10-14}$.

It should be apparent to a skilled worker that several additional sets and lbiraries of sets can be prepared in which the one or more polypeptide positions $Xaa^{10-14}$ or $Xaa^{13-17}$ is occupied by a single, known, predetermined residue and one or more other positions in each set are occupied by equimolar mixtures of the residues used. Several of those additional combinations are disclosed in U.S. patent applications Ser. No. 08/253,854 filed Jun. 3, 1994 and Ser. No. 07/943,709, filed Sep. 11, 1992, and PCT application WO 92/09300 published Jun. 11, 1992 (whose disclosures are incorporated by reference) for hexamer sets and libraries from which exemplary pentameric combinations useful here can be deduced.

Synthesis Processes

Two general approaches to synthesis of a polypeptide set are preferred for providing the desired equimolarity at the mixture positions of the set. One is referred to as the physical mixture process and the other is referred to as the chemical mixture process. Both approaches utilize a solid phase support such as a benzyhydrylamine (BHA) or methylbenzhydrylamine (MBHA) resin commonly used in solid phase peptide syntheses, as are discussed hereinbelow.

The physical mixture process utilized is that described in Houghten et al., Letters to Nature, 354:84–86 (1991); Pinnila et al., Vaccines 92, Cold Spring Harbor Laboratory Press, Cold Spring Harbor, pages 25–27 (1992); Appel et al., Immunomethods, 1:17–23 (1992); and WO 92/09300 published Jun. 11, 1992. These synthetic processes are also similar to the processes disclosed in Furka et al., Int. J. Peptide Protein Res., 37:487–493 (1991), Huebner et al. U.S. Pat. No. 5,182,366, incorporated by reference, and Lam et al., Letters to Nature, 355:82–84 (1991).

The latter two processes and that used herein differ in concept. In both Lam et al. and Huebner et al., the desired peptide is selected by its binding or reaction, recovered and then its sequence is determined. Furka et al. teach no reactions with their mixtures, so it is unknown how the authors intended those mixtures to be used. The present polypeptide sets are prepared with one or more known, predetermined residues at one or more known, predetermined positions along the polypeptide chain so that all one need do is determine which polypeptide of known sequence had the desired activity.

A chemical mixture synthesis of a polypeptide set can be one of those described in Rutter et al. U.S. Pat. No. 5,010, 175 or Geysen U.S. Pat. No. 5,194,392, whose disclosures are incorporated by reference, or as described in the previously noted published papers of which Geysen is an author. It is noted that the Geysen work does not utilize a cleavable bond between the solid support and polypeptide chain. Such a bond is preferred here and is synthesized as described hereinafter.

Both Rutter et al. and Geysen report using N-t-BOC protecting groups for their chemical mixture syntheses. Each of those patents provides an exemplary mixture of N-t-BOC-blocked amino acid derivatives for use in synthesis of equimolar amounts of amino acid residues.

It is noted that the present invention is not limited to use of N-t-BOC blocking groups for synthesis of polypeptide sets. This is the case whether the physical or chemical mixture approaches are utilized. Thus, any blocking group can be utilized. Table 1, below, provides mole ratios of blocked amino acids that can be used for a chemical mixture synthesis using Fmoc blocking group chemistry.

TABLE 1*

| Amino Acid | Mole Ratio |
|---|---|
| Ala | 0.22 |
| Asp (tBU ester) | 0.47 |
| Glu (tBU ester) | 0.62 |
| Phe | 0.35 |
| Gly | 0.20 |
| His (Tr) | 0.72 |
| Ile | 2.51 |
| Lys (tBoc) | 0.59 |
| Leu | 0.48 |
| Met | 0.34 |
| Asn | 1.65 |
| Pro | 0.20 |
| Gln | 2.03 |
| Arg (Mtr) | 1.98 |
| Ser (tBU ether) | 0.80 |
| Thr (tBU ether) | 2.18 |
| Val | 1.85 |

TABLE 1*-continued

| Amino Acid | Mole Ratio |
| --- | --- |
| Tyr ($^t$BU ether) | 0.81 |
| Trp | 0.99 |

*Parenthesized designations in the left column are protecting groups. $^t$BU = t-butyl; Tr = trityl; $^t$Boc = t-butyloxycarbonyl; Mtr = 4-methoxy-2,3,6-trimethylbenzenesulfonyl.

Substantial equimolarity in the mixture positions is typically within the limits of weighing accuracy using the physical mixture synthetic process because single amino acids are reacted in large excess and reactions are driven to completion. The chemical mixture process does not provide exact equimolarity as does the physical mixture process described before. For example, U.S. Pat. No. 5,010,175 reported variation from equimolarity in the range of 0.20–0.32 moles and an average of 0.25±0.04, with each amino acid being no more than 0.8 to 1.28 times the desired result. Deviations from equimolarity from that obtained with the physical mixture method of up to about 35 percent have been observed with no adverse effect. Regardless of the deviations from exact equimolarity observed from use of the chemical mixture method, the various polypeptides required to obtain enhanced binding by a corresponding polypeptide are present in large enough quantities to be useful in the assay methods discussed hereinafter.

It is thus seen that both physical and chemical mixture synthetic processes for preparing a desired precursor polypeptide set are well known in the art.

It is noted that cysteine and tryptophan are frequently omitted from polypeptide sets because of side reactions that can occur from their use. It has been found, however, that use of an N-formyl blocking group on tryptophan can alleviate much of the difficulty in synthesis when that residue is incorporated into a polypeptide chain. The N-formyl group can be removed during the usual side chain deprotecting step by the addition of a mercaptan-containing reagent such as ethanedithiol during the "low HF" deprotection reaction discussed herein.

It is further noted that one can use a wide range of solid supports for a contemplated synthesis of a polypeptide set. Usually used cross-linked styrene beads having benzhydrylamine groups are a preferred solid support. However, many other solid supports as are disclosed in U.S. Pat. No. 4,631,211 can also be utilized, as can a cellulosic support such as cotton as is described in Lebl et al. U.S. Pat. No. 5,202,418, both of whose disclosures are incorporated by reference.

In preferred practice, each polypeptide is coupled to the solid support during synthesis by a selectively severable covalent bond, such as an ester or an amide bond. An ultimately produced polypeptide mixture set is cleaved (separated or severed) from the solid support, and thereafter recovered.

Syntheses of polypeptide sets is preferably carried out using foraminous (porous) containers that are described in U.S. Pat. No. 4,631,211, whose disclosures are incorporated by reference. Another useful synthetic technique, particularly for use in the chemical mixture process, is the process described in Lebl et al. U.S. Pat. No. 5,202,418, whose disclosures are incorporated herein by reference.

Various useful solid supports, methods of their use, reagents for linking the growing polypeptide to the support, cleaving an polypeptide from the support and the like are well known to workers skilled in this art such that further exemplification is unnecessary. Further such exemplifications can, however, be found in U.S. Pat. No. 4,631,211 and in WO 92/09300, published Jun. 11, 1992, whose disclosures are incorporated by reference.

A complex mixture of solid support-coupled polypeptides, once deprotected and cleaved or severed from the solid support, is referred to herein as an polypeptide set, a polypeptide mixture set, by a similar phrase, or more simply as a "set". Being severed from the solid support, a polypeptide set is unsupported, and because of its method of synthesis, the polypeptide of such a set is linear.

The number of sets within a library of sets is determined by the number of different amino acid residues utilized at the single, known, predetermined position. Thus, where the twenty naturally occurring amino acid residues are used, each set contains 20 mixtures. The number of individual polypeptides in each mixture set is determined by multiplying the number of amino acid residues used at each equimolar mixture position.

It is virtually impossible to identify each polypeptide present in a mixture having the complexity of those polypeptide sets described herein. However, by using the synthetic methods discussed before, a skilled worker can construct a mixed polypeptide set, which upon hydrolysis and amino acid analysis has molar ratios of each amino acid used in the variable, expanded hinge region to each other in the range of about 0.5 to about 1.5; i.e., the molar ratio of one of those amino acid residues to any other residue is 1:1±about 0.5, more preferably, this ratio is 1:1±about 0.25, which ratios carry through to the linear polypeptides.

Each chain of a set is also present in an equimolar amount and is of the same length (contains the same number of residues) compared to the other chains present in the set. This equimolarity is also substantially impossible to measure directly. However, by carrying out each reaction to completion and maintaining the previously discussed equimolarity, one can prepare chains that are of the same length and are present in equimolar amounts.

Assay Processes

The present invention also contemplates a process for determining the sequence of a linear polypeptide that exhibits preferential (optimal) antimicrobial or hemolytic activity or catalyzes a hydrolytic reaction of a predetermined substrate molecule. A contemplated catalytic hydrolysis is also specific in that where a plurality of hydrolyzable bonds are present, preferably only one or a relatively few are cleaved, as compared to random cleavage provided by an aqueous medium. A contemplated process can be carried out with the sets coupled to the solid support used for synthesis or with those sets not coupled to the solid support used for synthesis, the latter being preferred.

In accordance with one such embodiment, an iterative process for determining the sequence of a linear polypeptide that exhibits preferential antimicrobial, hemolytic or catalytic hydrolysis of a predetermined substrate is contemplated. That process comprises the steps of:

(i) providing a library of a plurality of sets of linear polypeptides in which each set comprises a mixture of equimolar amounts of polypeptide member chains having the sequence Xaa¹Xaa²Xaa³GlyIleGlyAlaValLeuXaa¹⁰ValLeu—
Xaa¹³Xaa¹⁴Xaa¹⁵Xaa¹⁶Xaa¹⁷AlaLeuIleSer—
TrpIleLysArgXaa²⁶Xaa²⁷Xaa²⁸Xaa²⁹

(SEQ ID NO:2)

wherein for each polypeptide (a) each of $Xaa^1$, $Xaa^2$ and $Xaa^3$ is present or absent, with the provisos that $Xaa^2$ is present only if $Xaa^3$ is present, and $Xaa^1$ is present only if $Xaa^2$ is present;

(b) $Xaa^3$ when present is an amino acid residue selected from the group consisting of Asp, Glu, Asn, Gln, Ser, Lys and Arg;

(c) $Xaa^2$ when present is an amino acid residue selected from the group consisting of Asp, Glu, Asn, Gln, Ser, Lys and Arg;

(d) $Xaa^1$ when present is an amino acid residue selected from the group consisting of Ala, Val, Leu, Ile, Trp and Phe;

(e) $Xaa^{10}$ is an amino acid residue selected from the group consisting of Lys, Asp and Glu;

(f) $Xaa^{26}$, $Xaa^{27}$, $Xaa^{28}$ and $Xaa^{29}$ are present or absent, with the provisos that $Xaa^{27}$ is present only if $Xaa^{26}$ is present, $Xaa^{28}$ is present only if $Xaa^{27}$ is present, and $Xaa^{29}$ is present only if $Xaa^{28}$ is present;

(g) $Xaa^{26}$ when present is Lys, $Xaa^{27}$ when present is Arg, $Xaa^{28}$ when present is Gln and $Xaa^{29}$ when present is Gln—$NH_2$; and (h) each of $Xaa^{13}$, $Xaa^{14}$, $Xaa^{15}$, $Xaa^{16}$ and $Xaa^{17}$ is one of at least six different predetermined amino acid residues; and wherein for each said set:

(a') one or more of $Xaa^{13}$, $Xaa^{14}$, $Xaa^{15}$, $Xaa^{16}$ and $Xaa^{17}$ is the same, predetermined residue, present at the same one or more chain positions in each polypeptide; and (b') at least one other chain position occupied by $Xaa^{13}$, $Xaa^{14}$, $Xaa^{15}$, $Xaa^{16}$ and $Xaa^{17}$ contains an equimolar amount of those at least six different amino acid residues.

Each set of the library differs from the other sets in the identity of the one or more same predetermined residues present at the same one or more predetermined chain position within each set.

(ii) Each set from the library of sets is separately admixed with microbes, red blood cells or catalyst substrate in an aqueous medium at a set concentration of about 0.1 milligrams per liter to about 100 grams per liter. The antimicrobial, hemolytic or catalytic activity, respectively, exhibited by each set is separately assayed. A set exhibiting preferential activity relative to the other sets is determined, thereby identifying one or more amino acid residues that provided preferential antimicrobial, hemolytic or catalytic activity at said one or more predetermined positions.

(iii) A second library of sets identical to said first-named library of sets except for the polypeptide sequences at $Xaa^{13-17}$ is provided. That second library of sets contains the one or more amino acid residues of the first-named library identified as exhibiting preferential activity in the same one or more predetermined chain positions as in the sets of the first-named library. The member polypeptide chains of the sets of the second library have a predetermined one of the at least six different amino acid residues at another predetermined position within chain positions $Xaa^{13-17}$ different from the one or more positions of the identified one or more amino acid residues of the first-named library of sets. Each of the second library of sets has equimolar amounts of the at least six different amino acid residues of the first-named library of sets at the same one or more positions of the polypeptide chain positions $Xaa^{13-17}$ not occupied by the one or more identified amino acid residues or the predetermined amino acid residues, and has one fewer polypeptide positions occupied by equimolar amounts of at least six different amino acid residues than the first-named library of sets.

The second library of sets used in this iteration thus differs from the first library of sets in that at least two chain positions within the second set library are identified and predetermined (defined), and that second set library contains one fewer mixture positions than does the first set library.

(iv) Each set of the second library of sets is separately admixed with microbes, reb blood cells or catalyst substrate in an aqueous medium at a set concentration of about 0.1 milligrams per liter to about 100 grams per liter. The antimicrobial, hemolytic or catalytic activity, respectively, exhibited by each set is separately assayed, and the second set that exhibits preferential activity is determined, thereby identifying an amino acid residue that provides preferential antimicrobial, hemolytic or catalytic activity at that other predetermined position in the polypeptide chain.

(v) Steps (iii) and (iv) are repeated using zero through two further libraries of sets of linear polypeptides instead of the second plurality of sets or until preferential activity does not increase when a further library is assayed. Each further library of sets of linear polypeptides comprises a mixture of equimolar amounts of member linear polypeptide chains containing the same polypeptide sequence except for positions $Xaa^{13-17}$ as utilized in the first two named libraries of sets. The member chains of the sets of each further library contain the amino acid residues in the polypeptide chain positions of $Xaa^{13-17}$ that exhibited preferential activity in a library of sets used immediately before, and a predetermined one of those at least six different amino acid residues at another predetermined position within $Xaa^{13-17}$ of the polypeptide chain different from the positions of the identified amino acid residues of the library of sets used immediately before. Each set of the further library of sets has equimolar amounts of the at least six different amino acid residues of the first-named sets at the same one or more positions $Xaa^{13-17}$ of the polypeptide chain not occupied by the identified amino acid residues or the predetermined amino acid residues.

Each of those set libraries of the step (v) iterations differs from the immediately previous library by having one more defined (predetermined) position occupied by one of at least six predetermined residues, and one fewer predetermined repeating unit position occupied by equimolar amounts of at least six residues. Steps (iii) and (iv) can alternatively be repeated until the last library assayed does not exhibit an increase in preferential activity compared to the library assayed in the immediately preceding repeated assay. If that is the case, the sequence is determined, with the remaining one or two positions previously occupied by equimolar mixtures being occupied by a convenient residue of choice. This rarely occurs.

Typically, however, the process continues, and individual polypeptides are prepared and assayed as discussed hereinafter. For example, the particular position assayed can be a position of redundancy within a longer sequence whose other as yet undefined positions, once defined, are needed for activity. A more active or otherwise synthetically convenient residue is then used at the position where clearly preferential activity was not exhibited.

Thus, each subsequent library of sets contains each of the previously identified residues in the polypeptide chain position that exhibited preferential activity, as well as a preferably adjacent predetermined residue at a position in the polypeptide chain previously occupied by an equimolar mixture position. Each of those further library member sets also has the same sequence and termini as the first-named sets and has equimolar amounts of the at least six different amino acid residues of said first-named sets at the same one or more positions of the polypeptide chain not occupied by the identified amino acid residues or the predetermined amino acid residues.

It is preferred that the one or more predetermined positions of the libraries of (i) are at one or the other terminus of the Xaa$^{13-17}$ positions of the polypeptide chain, more preferably the N-terminus of that region; i.e., at Xaa$^{13}$ for SEQ ID NO:2. It is also preferred that each new predetermined position in subsequently used sets be in a position adjacent to the position whose amino acid residue was identified in the immediately previous assay. Thus, as each of steps (iii) and (iv) is repeated with new libraries of sets, one more position in the sequence becomes identified, and the sets contain one fewer mixture position.

(vi) Where the last-assayed library exhibits increased preferential activity compared to the library used immediately before and one position of the polypeptide chain that provides preferential activity is not identified, at least six; i.e., the number of different residues at a mixture position, polypeptide chains are provided in which each chain contains the same polypeptide sequence except for positions Xaa$^{13-17}$ as utilized in the first-named library of sets. Each polypeptide chain contains the identified amino acid residues in chain positions Xaa$^{13-17}$ that exhibited increased antimicrobial, hemolytic or catalytic activity in the immediately preceding assay of step (v) and a predetermined one of the at least six different amino acid residues at another predetermined position in the polypeptide chain different from the positions of the identified amino acid residues used in the immediately preceding assay of step (v).

(vii) Each of the at least six polypeptides of step (vi) is separately admixed with microbes, red blood cells or catalyst substrate in an aqueous medium at a polypeptide concentration of about 0.1 milligrams to about 100 grams per liter. The antimicrobial, hemolytic or catalytic activity, respectively, exhibited by each polypeptide is separately assayed. The polypeptide that exhibits preferential activity is determined, thereby determining the sequence of a linear polypeptide having preferential antimicrobial, hemolytic or catalytic activity.

Thus, in usual practice, once the preferential or optimal residues for all but the last position have been determined, at least six individual linear polypeptide chains are provided. These molecules contain the same melittin-related sequence as did the chains of the first-named library of sets, and contain the amino acid residues at positions Xaa$^{13-17}$ in the sequence determined by the above assays; i.e., the molecules contain each of the identified residues at its position that exhibited preferential activity in the previous assays, and one each of the at least six amino acid residues used at the final position. These at least six polypeptides are separately admixed with the substrate and assayed for preferential or optimal activity as discussed before. Determination of the residue that exhibits preferential activity as compared to the other residues assayed from the results of this group of assays provides the last residue of the sequence and thereby a sequence for the linear polypeptide that provides preferential activity.

In some instances, as noted before, preferential activity does not increase when a further library is assayed; i.e., as additional known residues are used in place of mixtures of residues. In this case, the preferential activity sequence is thus determined and it is unnecessary to utilize the at least six individual polypeptides as discussed above, using a convenient residue instead thereof. If preferential activity increases when each further library is used and assayed, the individual polypeptides discussed above are prepared and used.

The above assay process is particularly useful with sets prepared from the before-discussed 400 corresponding polypeptide sets in which two positions are of known sequence. Thus, after the first assay, the two N-terminal (Xaa$^{13}$ and Xaa$^{14}$) preferential residues are determined In step (iv), the third position is scanned for preferential, specific activity. This process is continued until the sequence of the N-terminal four residues at positions Xaa$^{13-17}$ is known. Individual polypeptides are then usually used to complete the determination of the overall preferential sequence by determining preferential activity for the last position of this exemplary polypeptide.

Another particularly preferred assay process discussed before is a scanning process that utilizes library sets prepared from precursor positional polypeptide sets, such as a particularly preferred library of 95 sets discussed before. Here, the process comprises the steps of:

(i) providing a library of a plurality of sets of linear polypeptides in which each set comprises a mixture of equimolar amounts of polypeptide member chains having the sequence Xaa$^1$Xaa$^2$Xaa$^3$GlyIleGlyAlaValLeuXaa$^{10}$ValLeu—
Xaa$^{13}$Xaa$^{14}$Xaa$^{15}$Xaa$^{16}$Xaa$^{17}$AlaLeuIleSer—
TrpIleLysArgXaa$^{26}$Xaa$^{27}$Xaa$^{28}$Xaa$^{29}$
(SEQ ID NO:2)

wherein for each polypeptide
(a) each of Xaa$^1$, Xaa$^2$ and Xaa$^3$ is present or absent, with the provisos that Xaa$^2$ is present only if Xaa$^3$ is present, and Xaa$^1$ is present only if Xaa$^2$ is present;
(b) Xaa$^3$ when present is an amino acid residue selected from the group consisting of Asp, Glu, Asn, Gln, Ser, Lys and Arg;
(c) Xaa$^2$ when present is an amino acid residue selected from the group consisting of Asp, Glu, Asn, Gln, Ser, Lys and Arg;
(d) Xaa$^1$ when present is an amino acid residue selected from the group consisting of Ala, Val, Leu, Ile, Trp and Phe;
(e) Xaa$^{10}$ is an amino acid residue selected from the group consisting of Lys, Asp and Glu;
(f) Xaa$^{26}$, Xaa$^{27}$, Xaa$^{28}$ and Xaa$^{29}$ are present or absent, with the provisos that Xaa$^{27}$ is present only if Xaa$^{26}$ is present, Xaa$^{28}$ is present only if Xaa$^{27}$ is present, and Xaa$^{29}$ is present only if Xaa$^{28}$ is present;
(g) Xaa$^{26}$ when present is Lys, Xaa$^{27}$ when present is Arg, Xaa$^{28}$ when present is Gln and Xaa$^{29}$ when present is Gln—NH$_2$; and (h) each of $Xaa^{13}$, $Xaa^{14}$, $Xaa^{15}$, $Xaa^{16}$ and $Xaa^{17}$ is one of at least six different predetermined amino acid residues; and wherein for each said set (a') one of $Xaa^{13}$, $Xaa^{14}$, $Xaa^{15}$, $Xaa^{16}$ and $Xaa^{17}$ is the same, predetermined residue, present at the same chain position in each polypeptide; and (b') at least one other chain position occupied by $Xaa^{13}$, $Xaa^{14}$, $Xaa^{15}$, $Xaa^{16}$ and $Xaa^{17}$ contains an equimolar amount of those at least six different amino acid residues, each set of this library differs from the other sets in the identity and chain position of the one same predetermined residue present at the same predetermined chain position within each set.

(ii) Each set from the library of sets is separately admixed with microbes, red blood cells or catalyst substrate in an aqueous medium at a set concentration of about 0.1 milligrams per liter to about 100 grams per liter, and the antimicrobial, hemolytic or catalytic activity, respectively, exhibited by each set is separately assayed. The residue that exhibited preferential activity at each of scanned positions $Xaa^{13-17}$ provides the sequence of a polypeptide that exhibits preferential antimicrobial, hemolytic or catalytic activity.

A more preferred set and library of sets used in either above iterative or scanning process utilizes a polypeptide of SEQ ID NO:3, whose $Xaa^7$ is most preferably Glu. The other sets of polypeptides discussed before can also be used in either of the above processes.

The above process utilizes a library of sets that have a single, known, predetermined residue at each of polypeptide positions $Xaa^{13-17}$ with all of the other chain positions within $Xaa^{13-17}$ occupied by equimolar amounts of the at least six residues used. The number of sets of this library is five times the number of residues utilized at the mixture positions so that both the identity and position in the peptide chain within $Xaa^{13-17}$ of the single, known, predetermined residue are different for the different sets.

This large library can thus also be viewed as a library of five positional libraries, and the process can be referred to as positional scanning. When so viewed, each positional library contains sets having equimolar mixtures at four identical positions of the chain such as each of chain positions $Xaa^{14-17}$, and one each of the known, predetermined at least six different residues used at polypeptide chain position $Xaa^{13}$. A second exemplary positional library of this group contains sets having equimolar mixtures at positions $Xaa^{13}$ and $Xaa^{15-17}$, with one each of the known, predetermined residues used in the mixtures at position $Xaa^{14}$. The third through fifth libraries contain sets having the single residue at chain position $Xaa^{14}$, $Xaa^{16}$ and $Xaa^{17}$, respectively, and equimolar mixtures of those residues at the remaining positions of $Xaa^{13-17}$ not occupied by the single residue.

That large library of sets can also be viewed as libraries of sets having the same, one known, predetermined residue at each of positions $Xaa^{13-17}$ and equimolar amounts of residues used at the other positions. As such, each library can be viewed as libraries whose five member sets share the identity of the one known, predetermined residue, with the number of libraries being at least six times the number of positions scanned, here five. These libraries differ in the identity of that one known, predetermined residue, whereas the sets of an above library differ as to the position of that one known, predetermined residue.

It should be apparent that sets of each of the positional or identity libraries can be assayed as described previously, and useful results obtained for each position and/or residue identity. The earlier-discussed process is thus a summary of individual assays of each of the positional or identity libraries.

Libraries of positional sets are preferred for use in that assaying of the activity of each library provides the identity of the most active one or more residues at that position. Carrying out a before-described process with libraries of positional sets is referred to as positional scanning, and is a preferred process because no order of assays need by followed to obtain a useful result.

In any assay discussed herein, all of the at least six different predetermined residues at a predetermined position can provide similar catalysis. That phenomenon is referred to as positional redundancy or redundancy, and any convenient residue is utilized at that position when a polypeptide catalyst is synthesized.

The aqueous medium used in an assay can be extremely varied and includes tap water, distilled or deionized water, as well as a buffer solution, a cell growth medium as is useful for culturing bacteria, yeast, fungi, plant or animal cells, all of which are well known to skilled workers. The same aqueous medium is used in each assay step within a given process.

The concentration of a linear polypeptide set in the aqueous medium is selected so that the polypeptide set is present at concentrations of about 0.1 milligrams per liter to about 100 grams per liter, preferably about 1.0 µg/ml to about 100 mg/ml, and more preferably about 0.1 µg/ml to about 20 mg/ml. Thus, when each polypeptide mixture is made up of 160,000 individual polypeptides; e.g. a set of polypeptides of SEQ ID NO:3, with one known residue and four mixture positions using the 20 natural amino acid residues, then each polypeptide within each mixture is present in a preferred concentration of about 1.0 µg/ml/160,000=6.2 pg/ml, to about 100 mg/ml/160,000=0.62 µg/ml. Presuming an average molecular weight of a set member polypeptide to be that of melittin itself, about 2850 g/mole, then at 1.0 µg/ml, the individual members of a set are present at a concentration of about 2.19 pmolar and at 100 mg/ml the individual members are present at about 0.22 µmolar. Most preferably, set concentrations of about 0.5 mg/ml to about 10 mg/ml are used.

When used as a catalyst, a contemplated polypeptide set is present in a catalytic amount. Such an amount is typically about 0.1 milligrams to about 1 gram per liter. The higher concentrations are usually used for antimicrobial or hemolytic compositions.

It is preferred, although not required, that a polypeptide mixture set be soluble in the aqueous medium utilized. Thus, the polypeptide sets are typically soluble in most aqueous media, whereas some sets with more hydrophobic alkyl groups form milky dispersions. Such dispersions are nonetheless useful, and a set can be utilized in an aqueous medium containing up to about volume percent of a water-miscible organic solvent such as methanol, ethanol, DMSO, acetone or DMF.

In assays for hemolytic activity, human red blood cells (erythrocytes) rather than cells of another animal are preferred. Assays involving microbes can utilize Gram-negative and Gram-positive bacteria as well as yeasts and fungi. The *E. coli* and *S. aureus* utilized herein are exemplary of such microbes that are otherwise well known, as are methods of culturing such microbes and assays for antimicrobial agents.

A contemplated polypeptide set, libraries of sets and individual polypeptides catalyze the hydrolysis of a predetermined substrate molecule.

Exemplary bonds hydrolyzed include carboxylic acid ester and amide bonds, phosphate ester bonds and also glycosyl ether bonds. In terms of enzyme-catalyzed hydrolyses, a contemplated set, library of sets and individual polypeptides broadly exhibit hydrolase activity, and an individual set can more specifically exhibit lipase, peptidase, phospholipase, nuclease or glycosidase activities.

The activity of a set can be assessed using any number of well known assays for hydrolytic activity that utilize well known or other substrates capable of undergoing a hydrolytic reaction. Exemplary substrate molecules are used in the examples hereinafter. Included among those substrates are N-tosyl-L-arginine methyl ester (TAMFE), N-benzoyl-L-tyrosine ethyl ester (BTEE) that are esterase substrates for trypsin and α-chymotrypsin, respectively; N-α-benzoyl-D, L-arginine p-nitroanilide (BAPNA), and N-succinyl-L-phenylalanine pnitroanalide that are amidase/peptidase substrates for trypsin and α-chymotrypsin, respectively; p-nitrophenyl-α-D-glucopyranoside, a substrate for β-glucosidase; and egg-yolk phosphatidylcholine (EPC), a substrate for phospholipase $A_2$. Various open-chain, circularized and nicked plasmids or open-chain polynucleotides can be used as substrates for nuclease (e.g. DNAase) activity. The same substrate molecule is also used for each assay in a given process.

The concentration of a substrate molecule can be quite varied, depending upon the contemplated use such as for kinetic studies or preparative work where the product of the hydrolysis is desired. Exemplary concentrations are provided hereinafter in the examples and can also be found in the before-discussed literature relating to peptide catalysis. Broadly, the concentrations range from the limit of solubility to the limit of detectability of the hydrolysis product.

Regardless of which of the above iterative or scanning processes is utilized, one has to make a choice as to which one or more residue(s) provided an optimal or preferential result so that a preferential or optimal sequence can be determined.

For an iterative process, a first line of demarcation is the activity of a prior sequence. Thus, adding an additional known predetermined residue to the sequence should enhance the activity. If the activity is not enhanced, the particular residue is not carried forward to the next iteration at that position.

Where an iteration enhances activity, one generally seeks to use the most active residue. However, if several residues have similarly enhanced activities, the easiest residues to work with are used; i.e., the cheapest, or a residue that requires no side chain blocking is used. Additionally, further separate sets can be prepared and used having different, but known residues at the same position when the activities of those residues were similar and more than about two to three times the activity of the next closest residue.

For a scanning process, a difference in activity of about a factor of two to three or more is usually sufficient to provide a clear cut advantage to a subsequently synthesized sequence by use of a residue providing such a difference. Thus, where one or a few residues provides a two- to three-fold activity enhancement over the other residues, those one or a few residues are utilized to prepare individual polypeptide molecules.

It is noted that a scanning process does not provide as precise results as does an iterative process. As a consequence, a few to tens of polypeptide sequences are frequently predicted as optimal sequences to be prepared and assayed as a result of a positional scanning process. That number is, of course, much fewer than the tens or hundreds of thousands of sequences that are eliminated by use of the process.

EXAMPLES

Example 1: Preparation of Mixture Sets

A library of sets of contemplated polypeptides was prepared in which the polypeptides corresponded in sequence to SEQ ID NO:3, wherein $Xaa^7$ is Glu, and wherein for the set, each of chain positions $Xaa^{11-14}$ was an equimolar amount of 19 of the 20 naturally occurring L-amino acid residues (all but Cys), and each set contained a different one of those residues at chain position $Xaa^{10}$. In preparing those sets, nineteen polypropylene mesh bags of p-methylbenzhydrylamine resin were prepared as described in U.S. Pat. No. 4,631,211. Common syntheses were carried out from the C-terminus to form 19 polypeptides having the residues of positions 15–26 of melittin and SEQ ID NO:3. These preparations were carried out using usually used solid phase synthesis techniques that are well known.

After removal of the 15-position N-terminal t-BOC group, the resin-linked peptides were reacted with a solution containing a mixture of the 19 activated L-amino acid derivatives noted hereinafter to provide the equimolar mixture of residues at position 14 by the before-discussed chemical mixture method. The solid and liquid phases were separated, the N-terminal t-BOC groups removed and the individual 19 resin-linked peptide mixtures were again reacted with the chemical mixture of 19 activated L-amino acids to provide an equimolar mixture of residues at chain position 13. This procedure was repeated twice more so that chain positions 12 and 11 were also prepared to contain equimolar mixtures of residues, thereby providing positions $Xaa^{11-14}$ as equimolar mixture positions.

The 19 separate bag-containing resin-linked mixtures so prepared were separately reacted with each one of the single 19 L-amino acid derivatives of the chemical mixture to provide the single, known, predetermined residue at position 10. The 19 mesh bags and their resin-linked peptide mixtures were thereafter reacted in common, together in the same solution, albeit each mixture was still in its own bag, to prepare the remainder of positions 9 through 1 of melittin and SEQ ID NO:3, except that position 7 was changed from Lys as is present in melittin to Glu. At the completion of the addition of residue 1, Gly, the 19 polypeptide mixtures were separately deblocked, cleaved from their solid supports as discussed hereinafter, and then recovered for use.

More specifically, aliquots of five grams (4.65 mmols) of p-methylbenzhydrylamine hydrochloride resin (MBHA) are placed into nineteen porous polypropylene bags (packets). These bags are placed into a common container and washed with 1.0 liter of $CH_2Cl_2$ three times (three minutes each time), then again washed three times (three minutes each time) with 1.0 liter of 5 percent DIEA/DCM (DIEA=diisopropylethylamine; $CH_2Cl_2$=DCM). The bags are then rinsed with DCM and placed into a common reaction vessel containing 50 ml (0.56M) of the respective t-BOC-amino acid/DCM-DMF (50/50) per bag or 950 ml. N,N-Diisopropylcarbodiimide (DIPCDI; 19×25 ml; 1.12M) is used as a coupling agent.

After one hour of vigorous shaking, Gisen's picric acid test [Gisen, *Anal. Chem. Acta*, 58:248–249 (1972)] is performed to determine the completeness of the coupling reaction. On confirming completeness of reaction, all of the resin packets are then washed with 1.5 liters of DMF and washed two more times with 1.5 liters of $CH_2Cl_2$.

The following steps are carried out in a common reaction vessel: (1) deprotection is carried out on the enclosed aliquots for thirty minutes with 1.5 liters of 55 percent TFA/DCM; and 2) neutralization is carried out with three washes of 1.5 liters each of 5 percent DIEA/DCM. Each bag is placed in a common solution of activated t-BOC-amino acid derivative and the coupling reaction carried out to completion as before. All coupling reactions are monitored using the above quantitative picric acid assay. This process can be repeated until position 15 of the sequence has been added.

The mixture of amino acid derivatives noted in Table 2, below, in 39.6 ml of dimethylformamide (DMF) is used for each coupling to prepare an equimolar mixture position, as about a 6-fold molar excess over the amount of amine present, as resin-amine or after deprotection to provide N-terminal amine (free amine) groups. One equivalent of DIPCDI as coupling agent and one equivalent of N-hydroxylbenztriazole-$H_2O$ are used per equivalent of mixed amino acid derivative, so both are also present in about a 6-fold excess over the free amine groups present.

TABLE 2[1]

| Amino Acid | Weight[2] |
|---|---|
| Ala | 140 mg |
| Asp (Bn) | 247 mg |
| Glu (Bn) | 268 mg |
| Phe | 146 mg |
| Gly | 110 mg |
| His (DNP) | 374 mg |
| Ile | 908 mg |
| Lys (Cl—CBZ) | 563 mg |
| Leu | 269 mg |
| Met | 133 mg |
| Asn | 271 mg |
| Pro | 203 mg |
| Gln | 286 mg |
| Arg (Tsl) | 609 mg |
| Ser (Bn) | 179 mg |
| Thr (Bn) | 323 mg |
| Val | 533 mg |
| Trp | 274 mg |
| Tyr (Br—CBZ) | 446 mg |

[1]Parenthesized designations in the left column are used by each unless another parenthesized protecting group is shown. Bn = benzyl; DNP = dinitrophenyl; Tsl = toluenesulfonyl; CBZ = benzyloxy carbonyl; Cl—CBZ = o-chlorobenzyloxy carbonyl; Br—CBZ = o-bromobenzyloxy carbonyl.
[2]Milligrams (mg) of each protected amino acid derivative present in a chemical mixture per 3.58 milliequivalent of resin —$NH_2$ group. Diisopropylcarbodiimide (DIPCD) used as coupling agent.

Each coupling is carried out at room temperature until there are no remaining free amine groups; about one hour. Each position of the precursor polypeptide containing equimolar amounts of amino acid residues is added as described above.

The fully protected solid support-coupled polypeptide mixtures are treated with 55 percent trifluoroacetic acid in methylene chloride prior to the HF treatment to remove the final t-BOC-protecting group. Then the protected solid support-coupled polypeptide mixtures, in polypropylene mesh packets [Houghten, *Proc. Natl. Acad. Sci., USA*, 82:5131–5135 (1985)] are rinsed with alternating washes of DCM and isopropanol, and dried under reduced pressure for twenty-four hours.

The low HF support cleavage step [Tam et al., *J. Am. Chem. Soc.*, 195:6442–6455 (1983)] is carried out in a two liter polypropylene reaction vessel, using a solution of 60 percent dimethylsulfide, 25 percent HF, 10 percent p-cresol and 5 percent ethylenedithiol. The ethanedithiol is used to cleave the N-formyl groups from tryptophan residues. Where it is desired not to cleave the N-formyl groups, ethanedithiol is omitted from the mixture and its amount is replaced by HF. $N_\alpha$-t-BOC-N-formyl tryptophan is available from Bachem, Inc., Torrence, Calif.

HF is condensed at −78° C. After condensation, the HF-scavenger solution is carefully transferred to the reaction vessel that contained the resin-containing packets. The low HF solution is made to give 5 ml per 0.1 mmol of polypeptide. After the reagents are added, the reaction vessel is placed in an ice water bath and shaken for two hours. The low HF solution is removed and the packets containing the deprotected peptide resins are quickly washed with chilled DCM. The DCM wash is repeated nine times (one minute each) followed by ten alternating washes of isopropanol and DCM. Finally, the resin is washed five times with DMF, then twice more with DCM. Deprotected peptide resin packets are dried under reduced pressure. After this process is completed, the unprotected peptides are ready to be cleaved by anhydrous HF.

Use of a benzhydrylamine resin as a solid support and anhydrous HF/anisole for cleavage of the polypeptide mixture set provides the desired C-terminal amido group for the polypeptide mixture set produced.

Example 2: Polypeptide Conformation by CD Spectroscopy

The library of sets of Example 1 was examined for the ability of each set to adopt an α-helical conformation. Each of the sets was found to adopt more than 80 percent α-helix in 65 percent trifluoroethanol in water, a solvent known to promote α-helices in potentially α-helical polypeptides. In the presence of 100 mM NaCl, the percent of α-helices varied from 20 to 40 percent. Melittin exhibits about 20 percent helicity under those conditions.

All measurements were carried out on a Jasco J-720 circular dichroism spectropolarimeter (CD-Eaton, Md.), in conjunction with a Neslab RTE 110 waterbath and temperature controller at 25° C. (Dublin, Calif.). CD spectra were the average of a series of three to seven scans made at 0.2 nm intervals. Ellipticity was determined as means residue ellipticity, θ; the limits of error of measurements at 222 nm were ±500 (deg cm2 dmol$^{-1}$). For salt induced aggregation, stock solutions were separately prepared with 150 μM polypeptide sets in buffer (5 mM MOPS-NaOH, 100 mM NaCl).

Example 3: Antimicrobial Activity Against *S. aureus*

The polypeptide libraries of Example 1 were assayed for activity against *Staphylococcus aureus* [(ATCC 29213); ATCC, 12301 Parklawn Drive, Rockville, Md.]. The results of those assays indicated that replacement of melittin's position-10 Thr by an arginine or lysine provided $IC_{50}$ values of 34 or 49 μg/ml, respectively, with each of the other replacements providing less than one-half the activity of arginine. U.S. Pat. No. 5,235,038 reported the lowest concentration of peptide at which there was no change in optical density over 18 hours (minimum inhibitory concentration—MIC) having a value of 25 μg/ml for melittin, measured under slightly different conditions.

To initiate the exponential phase of bacterial growth prior to the assay, a sample of bacteria grown overnight (about 18 hours) at 37° C. in Mueller Hinton broth (MH-Becton Dickinson Microbiology Systems) was reinoculated and incubated at 37° C. A final concentration of $10^5$ to $5 \times 10^5$ colony-forming units (CFU)/ml was used in all assays, vortexed and diluted 10-fold in Yeast Media (YM) broth (Difco Laboratories, Detroit, Mich.), for an approximate final concentration of $10^5$ to $5 \times 10^5$ CFU/ml. The assays were carried out in 96-well tissue culture plates (Costar, Pleasanton, Calif.), as described in Blondelle et al., Biochem., 31:12688–12694 (1992). In brief, a bacterial suspension in 2x broth was added to the polypeptides mixture sets at concentrations derived from serial two-fold dilutions varying from 1000 μg/ml to 4 μg/ml. The plates were then incubated 21 hours at 37° C. The relative percent growth of the bacteria was determined by the optical density at 620 nm ($OD_{620}$) using a Titertek Multiskan Plus apparatus (Flow Laboratories, McLean, Va.). The concentration necessary to inhibit 50 percent bacterial growth ($IC_{50}$) was then calculated using the software program Graphpad (ISI, San Diego, Calif.).

As should be apparent from the previous discussion, the iterative approach can be utilized to provide the sequence of an optimal or preferential antimicrobial polypeptide.

Example 4: Hemolytic Activity

As noted earlier, melittin is itself quite hemolytic. It was therefore of interest to ascertain whether a polypeptide mixture set such as that of Example 1 would exhibit greater or less hemolytic activity, particularly for those substitutions that exhibited enhanced α-helicity.

The results of this study indicated that whereas the $HD_{50}$ value for melittin itself was 6 μg/ml, the most active polypeptide set exhibited a $HD_{50}$ value of 10 μg/ml for Trp, with sets having eleven different residues at position $Xaa^{13}$ of SEQ ID NO:2 ranging within a factor of two of that value; i.e., up to about 20 μg/ml. The order of lessening activity for these sets is as follows, with the $HD_{50}$ value in μg/ml in parentheses: Trp (10), Tyr (12), Arg (13), Leu (15), Ser (16), Phe (17), Met (17), Lys (17), Thr (18), Ile (19) and Val (20).

The hemolytic activities of the polypeptide mixture sets were determined by using human red blood cells (RBCs). The cells were washed three times with phosphate-buffered saline (PBS/35 mM phosphate buffer—0.15M NaCl, pH 7.0) and resuspended in PBS. The hemolytic activity of the polypeptide sets were determined as described in Blondelle et al., Biochem. Biophys. Acta, 1202:331–336 (1993) using 96 well tissue culture plates. In brief, 100 μl of 0.5 percent RBC solution were added to an equal volume of peptides in PBS. The plates were incubated for one hour at 37° C. and the optical density (OD) of the supernatant was measured at 414 nm. The concentration in peptide necessary to lyse 50 percent RBCs ($HD_{50}$) was then determined for each peptide using a sigmoidal curve fitting method (Graphpad).

As should be apparent from the previous discussion, provision and similarly assaying the remaining seventy-six positional sets of this library using the positional scanning approach provides the sequence of a melittin-related polypeptide that exhibits optimal or preferential hemolysis in the above reaction.

Example 5: Trypsin-Like and α-Chymotrypsin-Like Activity

The polypeptide sets of Example 1 were assayed for trypsin-like and α-chymotrypsin-like peptidase activities using N-α-benzoyl-D,L-arginine p-nitroanilide and N-succinyl-L-phenylalanine p-nitroanilide, respectively. Each of the 19 sets of Example 1 was admixed and assayed at 0.19 mM in 59 mM MOPS buffer using 0.29 mM of substrate in the presence of 10 mM $CaCl_2$. Samples were incubated at 37° C. Substrate hydrolysis was monitored by UV spectroscopy at 406 nm, with solution turbidity at 500 nm being subtracted for each measurement.

The most active sets exhibited an optical density (OD) increase about one-tenth that exhibited by 0.1 μM trypsin, under similar conditions. Also using similar conditions, the observed OD increase was about equal to that provided by 0.1 μM α-chymotrypsin.

More specifically, mixtures sets of Example 1 having Ala, Asp, Glu and Lys as the known, single, predetermined residue exzhibited trypsin-like activity after 123 hours in excess of that shown in the absence of any polypeptide. Each of the ninetten sets exhibited greater α-chymotrypsin-like activity after 162 hours than shown by spontaneous, random cleavage of the substrate, with the above foud residues again providing the greatest activity. It is noted that sets containing Ala, Asp and Glu also exhibited precipitation.

As should be apparent from the previous discussion, the iterative approach can be utilized to provide the sequence of an optimal or preferential hydrolytic catalyst polypeptide.

Example 6: Glucosidase-like Activity

The glucosidase-like activity of the sets of Example 1 was monitored by the release of p-nitrophenol (increase in OD at 400 nm) from the substrate p-nitrophenol-α-D-glucopyranoside (PNPG). Each polypeptide mixture set was assayed at 0.19 mM in 50 mM MOPS buffer with 1.25 mM of PNPG. The samples were incubated at 37° C. The solution turbidity measured at 500 nm was subtracted from each measurement as described above.

The most active polypeptide mixture sets resulted in OD increment approximately 7-fold lower as compared to 1.4× $10^3$ unit/ml glucosidase of the 70 hours. The most active mixture sets contained Lys, Asp and Arg at the position of the single, known, predetermined residue, and exhibited precipitation.

As should be apparent from the previous discussion, provision and similarly assaying the remaining seventy-six positional sets of this library using the positional scanning approach provides the sequence of a melittin-related polypeptide that exhibits optimal or preferential catalysis in the above reaction.

Example 7: Further Peptidase Activity

Although amidase activity of a mixture set was illustrated in Example 5, a further study using the 31-mer polypeptide β-endorphin was carried out here using only three sets of Example 1. Those three sets contained His, Lys or Gln at the peptide position occupied by the single, known amino acid residue.

Each polypeptide mixture set was assayed at 0.66 mM in the presence of 0.22 mM β-endorphin and 10 mM $CaCl_2$ in 50 mM MOPS buffer. The samples were incubated at 37° C. up to four days. The reaction was monitored by disappearance of the RP-HPLC peak of β-endorphin and appearance of new peaks. The fractions corresponding to the new peaks were collected and the molecular weight of the new compounds determined by mass spectroscopy. Sequencing of those compounds is in progress.

Initial results indicate that each of the sets causes hydrolysis in excess of the relatively random spontaneous hydrolysis observed. In addition, the set having Lys as its known, single predetermined residue was most active.

As should be apparent from the previous discussion, the iterative approach can be utilized to provide the sequence of an optimal or preferential hydrolytic catalyst polypeptide.

Example 8: Phospholipase ($PLA_2$)-Like Activity

Phospholipase ($PLA_2$)-like activity of the sets was assayed by the release of lysophosphatidylcholine and fatty acid (oleic acid) from egg-yolk phosphatidylcholine (EPC) as substrate in the presence of various calcium ion concentrations and measured by HPLC. Calcium ion effects were assayed at zero, 3, 6, 12 and 20 mM, with 6 mM providing the greatest hydrolytic activity, and thus being the concentration for use.

Here, the polypeptide set concentration was 140 μM in MOPS 50 mM buffer at a pH value of 7, with an EPC concentration of 3 mM so that the molar ratio EPC/mixture set was about 22. A Nova-Pak silica gel HPLC column was used with an elution solvent of acetonitrile/methanol/water (50/50/3 v/v/v) and detection by a differential refractometer.

Sets having Asp, Glu, Gly, His, Asn, Pro, Gln and Ser provided between 60 and 80 percent hydrolysis after 10 days of incubation at 37° C. All of the other sets exhibited catalyzed hydrolyses of up to about 30 percent, except those having Arg and Thr that exhibited between about 30 and about 50 percent hydrolysis under these conditions.

As should be apparent from the previous discussion, provision and similarly assaying the remaining seventy-six positional sets of this library using the positional scanning approach provides the sequence of a melittin-related polypeptide that exhibits optimal or preferential catalysis in the above reaction.

Example 9: DNAase-Like Activity

Each of the polypeptide mixture sets of Example 1 was admixed at 70 μM with the pUC-18 plasmid at 5 μg/100 μl in a buffer comprised of 5 mM MOPS, 200 mM NaCl and 5 mM $MgCl_2$ of pH 7.9. Following incubation at 37° C. for 14 hours, the hydrolysis patterns of Table 3 were observed using agarose gel electrophoresis:

TABLE 3

| Known Residue | Hydrolysis Pattern[1] |
|---|---|
| Ala | Only 1, no 2 |
| Asp | Only 1, no 2 |
| Glu | Enhanced 1, some 2 |
| Gly | Enhanced 1, no 2 |
| Ile | No reaction |
| Asn | Enhanced 1, no 2 |
| Gln | No reaction |
| Val | No reaction |
| Melittin (control) | Enhanced 1, no 1 |

[1]Hydrolysis Patters are:
1 = open circularly relaxed plasmid bearing one cut in one DNA strand, but with retained circularity;
2 = linear plasmid indicating a double cut in the two DNA strands; and
No reaction: pattern unchanged from control pUC-18 in having some circularly covalently closed and some open circularly relaxed form present.

As should be apparent from the previous discussion, the iterative approach can be utilized to provide the sequence of an optimal or preferential hydrolytic catalyst polypeptide.

The foregoing is intended as illustrative of the present invention but not limiting. Numerous variations and modifications may be effected without departing from the true spirit and scope of the novel concepts of the invention.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 26
        ( D ) OTHER INFORMATION: /note= "The Xaa in the 26th position is a Gln-NH2 residue."

( x i ) SEQUENCE DESCRIPTION: SEQ ID NO:1:

Gly Ile Gly Ala Val Leu Lys Val Leu Thr Thr Gly Leu Pro Ala Leu
1               5                   10                  15

Ile Ser Trp Ile Lys Arg Lys Arg Gln Xaa
                20                  25

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: peptide ( i x ) FEATURE:
  ( A ) NAME/KEY: Peptide
  ( B ) LOCATION: 1..29
  ( D ) OTHER INFORMATION: /note= "(a) each Xaa in the first,
    second and third positions is present or absent, but Xaa
    in the second position is present only if Xaa in the
    third position is present, and Xaa in the first position
    is present only if Xaa in the second position is present;
    ( b ) Xaa in the third position, when present, is an amino
    acid residue selected from the group consisting of Asp,
    Glu, Asn, Gln, Ser, Lys and Arg;
    ( c ) Xaa in the second position, when present, is an
    amino acid residue selected from the group consisting
    of Asp, Glu, Asn, Gln, Ser, Lys and Arg;
    ( d ) Xaa in the first position, when present, is an amino
    acid residue selected from the group consisting of Ala,
    Val, Leu, Ile, Trp and Phe;
    ( e ) Xaa in the tenth position is an amino acid residue
    selected from the group consisting of Lys, Asp and Glu;
    ( f ) Xaa in the twenty-sixth, twenty-seventh, twenty-
    eighth and twenty-ninth positions are present or absent,
    but Xaa in the twenty-seventh position is present only if
    Xaa in the twenty-sixth position is present, Xaa in the
    twenty- eighth position is present only if Xaa in the
    twenty- seventh position is present, and Xaa in the
    twenty- ninth position is present only if Xaa in the
    twenty- eighth position is present;
    ( g ) Xaa in the twenty-sixth position, when present,
    is Lys, Xaa in the twenty-seventh position, when
    present, is Arg, Xaa in the twenty-eighth position,
    when present, is Gln and Xaa in the twenty-ninth
    position, when present, is Gln-NH2; and
    ( h ) each of Xaa in the thirteenth, fourteenth,
    fifteenth, sixteenth and seventeenth positions is one of
    at least six different predetermined amino acid residues
    selected from the group consisting of RNA encoded L-amino
    acid residues, a corresponding D-amino acid residue, L
    and D-forms of 2-aminoadipic acid, 3-aminoadipic acid,
    beta- alanine, 2-aminobutyric acid, 4-aminobutyric acid,
    6- aminocaproic acid, 2-aminoheptanoic acid, 2-aminoiso-
    butyric acid, 3-aminoisobutyric acid, 2-aminopimelic
    acid, 2,4- diaminobutyric acid, desmosine, 2,2'-diamino-
    pimetic acid, 2,3-diaminopropionic acid, N-ethylglycine,
    N- ethylasparagine, hydroxylysine, allo-hydroxylysine,
    3- hydroxyproline, 4-hydroxyproline, isodesmosine, allo-
    isoleucine, sarcosine, N-methylisoleucine, N-methyl-
    valine, norvaline, norleucine, ornithine, and
    penicillamine."

( x i ) SEQUENCE DESCRIPTION: SEQ ID NO:2:

```
Xaa  Xaa  Xaa  Gly  Ile  Gly  Ala  Val  Leu  Xaa  Val  Leu  Xaa  Xaa  Xaa  Xaa
1                  5                             10                           15

Xaa  Ala  Leu  Ile  Ser  Trp  Ile  Lys  Arg  Xaa  Xaa  Xaa  Xaa
               20                       25
```

( 2 ) INFORMATION FOR SEQ ID NO:3:

( i ) SEQUENCE CHARACTERISTICS:
  ( A ) LENGTH: 26 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Peptide
  ( B ) LOCATION: 1..26
  ( D ) OTHER INFORMATION: /note= "(a) Xaa in the seventh
    position is an amino acid residue selected from the
    group consisting of Lys, Asp and Glu;
    ( b ) each of Xaa in the tenth, eleventh, twelfth,
    thirteenth and fourteenth positions is one of at least
    six amino acids; and selected from the group consisting
    of RNA encoded L-amino acid residues, a corresponding
    D-amino acid residue, L and D-forms of 2-aminoadipic
    acid, 3- aminoadipic acid, beta-alanine, 2-aminobutyric -continued

```
       acid, 4- aminobutyric acid, 6-aminocaproic acid, 2-amino-
       heptanoic acid, 2-aminoisobutyric acid, 3-amino-
       isobutyric acid, 2-aminopimelic acid, 2,4-diaminobutyric
       acid, desmosine, 2,2'-diaminopimetic acid, 2,3-diamino-
       propionic acid, N-ethylglycine, N-ethylasparagine,
       hydroxylysine, allo-hydroxylysine, 3-hydroxyproline,
       4- hydroxyproline, isodesmosine, allo-isoleucine,
       sarcosine, N- methylisoleucine, N-methylvaline,
       norvaline, norleucine, ornithine, and penicillamine; and
       ( c ) Xaa in the twenty-sixth position is Gln-NH2."
```

( x i ) SEQUENCE DESCRIPTION: SEQ ID NO:3:

```
Gly  Ile  Gly  Ala  Val  Leu  Xaa  Val  Leu  Xaa  Xaa  Xaa  Xaa  Xaa  Ala  Leu
 1              5                         10                        15

Ile  Ser  Trp  Ile  Lys  Arg  Leu  Arg  Gln  Xaa
              20                        25
```

We claim:

1. A process for determining the sequence of a linear polypeptide that exhibits preferential antimicrobial, hemolytic or catalytic hydrolysis of a predetermined substrate comprising the steps of:

(i) providing a library of a plurality of sets of linear polypeptides in which each set comprises a mixture of equimolar amounts of polypeptide member chains having the sequence $Xaa^1Xaa^2Xaa^3GlyIleGlyAlaValLeuXaa^{10}ValLeu$
$Xaa^{13}Xaa^{14}Xaa^{15}Xaa^{16}Xaa^{17}AlaLeuIleSerTrp$
$IleLysArgXaa^{26}Xaa^{27}Xaa^{28}Xaa^{29}$ (SEQ ID NO:2)

wherein for each polypeptide (a) each of $Xaa^1$, $Xaa^2$ and $Xaa^3$ is present or absent, with the provisos that $Xaa^2$ is present only if $Xaa^3$ is present, and $Xaa^1$ is present only if $Xaa^2$ is present;

(b) $Xaa^3$ when present is an amino acid residue selected from the group consisting of Asp, Glu, Asn, Gln, Ser, Lys and Arg;

(c) $Xaa^2$ when present is an amino acid residue selected from the group consisting of Asp, Glu, Asn, Gln, Ser, Lys and Arg;

(d) $Xaa^1$ when present is an amino acid residue selected from the group consisting of Ala, Val, Leu, Ile, Trp and Phe;

(e) $Xaa^{10}$ is an amino acid residue selected from the group consisting of Lys, Asp and Glu;

(f) $Xaa^{26}$, $Xaa^{27}$, $Xaa^{28}$ and $Xaa^{29}$ are present or absent, with the provisos that $Xaa^{27}$ is present only if $Xaa^{26}$ is present, $Xaa^{28}$ is present only if $Xaa^{27}$ is present, and $Xaa^{29}$ is present only if $Xaa^{28}$ is present;

(g) $Xaa^{26}$ when present is Lys, $Xaa^{27}$ when present is Arg, $Xaa^{28}$ when present is Gln and $Xaa^{29}$ when present is Gln—$NH_2$; and (h) each of $Xaa^{13}$, $Xaa^{14}$, $Xaa^{15}$, $Xaa^{16}$ and $Xaa^{17}$ is one of at least six different predetermined amino acid residues; and wherein for each said set (a') one of $Xaa^{13}$, $Xaa^{14}$, $Xaa^{15}$, $Xaa^{16}$ and $Xaa^{17}$ is the same, predetermined residue, present at the same chain position in each polypeptide; and (b') at least one other chain position occupied by $Xaa^{13}$, $Xaa^{14}$, $Xaa^{15}$, $Xaa^{16}$ and $Xaa^{17}$ contains an equimolar amount of said at least six different amino acid residues, each set of said library differing from the other sets in the identity and chain position of said one same predetermined residue present at the same predetermined chain position within each set; and (ii) separately admixing each set from said library of sets with microbes, red blood cells or catalyst substrate in an aqueous medium at a set concentration of about 0.1 milligrams per liter to about 100 grams per liter, and separately assaying the antimicrobial, hemolytic or catalytic activity, respectively, exhibited by each set, the residue that exhibited preferential activity at each of positions $Xaa^{13-17}$ providing the sequence of a polypeptide that has preferential antimicrobial, hemolytic or catalytic activity in the assay used.

2. The process according to claim 1 wherein said single predetermined amino acid residue of each polypeptide chain at positions $Xaa^{13-17}$ is one of about 10 to about 15 different amino acid residues, and the same about 10 to about 15 different amino acid residues are present in equimolar amounts at the other $Xaa^{13-17}$ chain positions of the set.

3. The process according to claim 2 wherein each of said sets is provided not coupled to a solid support used for synthesis.

4. The process according to claim 1 wherein $Xaa^3$ is absent.

5. The process according to claim 4 wherein $Xaa^{29}$ is present.

6. A process for determining the sequence of a linear polypeptide that exhibits preferential antimicrobial, hemolytic or catalytic hydrolysis of a predetermined substrate comprising the steps of:

(i) providing a library of a plurality of sets of linear polypeptides in which each set comprises a mixture of equimolar amounts of polypeptide member chains having the sequence $Xaa^1Xaa^2Xaa^3GlyIleGlyAlaValLeuXaa^{10}ValLeu-$
$Xaa^{13}Xaa^{14}Xaa^{15}Xaa^{16}Xaa^{17}AlaLeuIleSer-$
$TrpIleLysArgXaa^{26}Xaa^{27}Xaa^{28}Xaa^{29}$
(SEQ ID NO:2)

wherein for each polypeptide (a) each of $Xaa^1$, $Xaa^2$ and $Xaa^3$ is present or absent, with the provisos that $Xaa^2$ is present only if $Xaa^3$ is present, and $Xaa^1$ is present only if $Xaa^2$ is present;

(b) $Xaa^3$ when present is an amino acid residue selected from the group consisting of Asp, Glu, Asn, Gln, Ser, Lys and Arg;

(c) $Xaa^2$ when present is an amino acid residue selected from the group consisting of Asp, Glu, Asn, Gln, Ser, Lys and Arg;

(d) $Xaa^1$ when present is an amino acid residue selected from the group consisting of Ala, Val, Leu, Ile, Trp and Phe;

(e) $Xaa^{10}$ is an amino acid residue selected from the group consisting of Lys, Asp and Glu;

(f) $Xaa^{26}$, $Xaa^{27}$, $Xaa^{28}$ and $Xaa^{29}$ are present or absent, with the provisos that $Xaa^{27}$ is present only if $Xaa^{26}$ is present, $Xaa^{28}$ is present only if $Xaa^{27}$ is present, and $Xaa^{29}$ is present only if $Xaa^{28}$ is present;

(g) $Xaa^{26}$ when present is Lys, $Xaa^{27}$ when present is Arg, $Xaa^{28}$ when present is Gln and $Xaa^{29}$ when present is Gln—$NH_2$; and (h) each of $Xaa^{13}$, $Xaa^{14}$, $Xaa^{15}$, $Xaa^{16}$ and $Xaa^{17}$ is one of at least six different predetermined amino acid residues; and wherein for each said set:

(a') one or more of $Xaa^{13}$, $Xaa^{14}$, $Xaa^{15}$, $Xaa^{16}$ and $Xaa^{17}$ is the same, predetermined residue, present at the same one or more chain positions in each polypeptide; and (b') at least one other chain position occupied by $Xaa^{13}$, $Xaa^{14}$, $Xaa^{15}$, $Xaa^{16}$ and $Xaa^{17}$ contains an equimolar amount of said at least six different amino acid residues, each set of said library differing from the other sets in the identity of said one or more same predetermined residues present at the same one or more predetermined chain position within each set; and (ii) separately admixing each set from said library of sets with microbes, red blood cells or catalyst substrate in an aqueous medium at a set concentration of about 0.1 milligrams per liter to about 100 grams per liter, separately assaying the antimicrobial, hemolytic or catalytic activity, respectively, exhibited by each set, and determining a set exhibiting preferential activity relative to the other sets, thereby identifying one or more amino acid residues that provided preferential activity at said one or more predetermined positions;

(iii) providing a second library of sets identical to said first-named library of sets except for the polypeptide sequences at $Xaa^{13-17}$, said second library of sets containing the one or more amino acid residues of the first-named library identified as exhibiting preferential activity in the same one or more predetermined chain positions as in the sets of the first-named library, the member polypeptide chains of the sets of said second library having a predetermined one of said at least six different amino acid residues at another predetermined position within chain positions $Xaa^{13-17}$ different from said one or more positions of the identified one or more amino acid residues of the first-named library of sets, each of said second library of sets having equimolar amounts of said at least six different amino acid residues of said first-named library of sets at the same one or more positions of the polypeptide chain positions $Xaa^{13-17}$ not occupied by said one or more identified amino acid residues or the predetermined amino acid residues, and having one fewer polypeptide positions occupied by equimolar amounts of at least six different amino acid residues than said first-named library of sets;

(iv) separately admixing each set of said second library of sets with microbes, red blood cells or catalyst substrate in an aqueous medium at a set concentration of about 0.1 milligrams per liter to about 100 grams per liter, separately assaying the antimicrobial, hemolytic or catalytic activity, respectively, exhibited by each set, and determining a second set exhibiting preferential activity relative to the other assayed sets, thereby identifying an amino acid residue that provides preferential activity at said other predetermined position in the polypeptide chain;

(v) repeating steps (iii) and (iv) using zero through two further libraries of sets of linear polypeptides instead of said second plurality of sets or until preferential activity does not increase when a further library is assayed, each further library of sets of linear polypeptides comprising a mixture of equimolar amounts of member linear polypeptide chains containing the same polypeptide sequence except for positions $Xaa^{13-17}$ as utilized in the first two named libraries of sets, the member chains of the sets of each further library containing the amino acid residues in the polypeptide chain positions that exhibited preferential activity in a library of sets used immediately before, and a predetermined one of said at least six different amino acid residues at another predetermined position within $Xaa^{13-17}$ of the polypeptide chain different from the positions of the identified amino acid residues of the library of sets used immediately before, each of said further libraries of sets having equimolar amounts of said at least six different amino acid residues of said first-named sets at the same one or more positions $Xaa^{13-17}$ of the polypeptide chain not occupied by the identified amino acid residues or the predetermined amino acid residues;

(vi) where the last-assayed library of sets exhibits increased preferential antimicrobial, hemolytic or catalytic activity compared to the library used immediately before and one position of the polypeptide chain that provides preferential activity is not identified, providing at least six polypeptide chains in which each chain contains the same polypeptide sequence except for positions $Xaa^{13-17}$ as utilized in the first-named libraries of sets, each polypeptide chain containing the identified amino acid residues in the polypeptide chain positions that exhibited increased preferential activity in the immediately preceding assay of setp (v) and a predetermined one of said at least six different amino acid residues at another predetermined position in the polypeptide chain different from the positions of the identified amino acid residues used in the immediately preceding assay of step (v); and (vii) separately admixing each of said at least six polypeptides of setp (vi) with microbes, red blood cells or catalyst substrate in an aqueous medium at a polypeptide concentration of about 0.1 milligrams to about 100 grams per liter, separately assaying antimicrobial, hemolytic or catalytic activity, respectively, of each polpeptide, and determining the polypeptide exhibiting preferential activity thereby determining the sequence of a linear polypeptide that provides preferential activity.

7. The process according to claim 6 wherein each of said sets is provided not coupled to a solid support used for synthesis.

8. The process according to claim 6 wherein $Xaa^3$ is absent.

9. The process according to claim 8 wherein $Xaa^{29}$ is present.

* * * * *